United States Patent
Beadle et al.

(10) Patent No.: US 12,377,338 B2
(45) Date of Patent: Aug. 5, 2025

(54) MODULAR METRICS BAR FOR AN EXERCISE MACHINE

(71) Applicant: Nautilus, Inc., Vancouver, WA (US)

(72) Inventors: Kristin A. Beadle, Portland, OR (US); Wesley Citti, Portland, OR (US); James Tsai, Camas, WA (US); Heather Marshall, Portland, OR (US); Robert Nicholas Haselmann, Eden Prairie, MN (US); Joshua Hammond Harling, Portland, OR (US)

(73) Assignee: Johnson Health Tech Retail, Inc., Cottage Grove, WI (US)

( * ) Notice: Subject to any disclaimer, the term of this patent is extended or adjusted under 35 U.S.C. 154(b) by 237 days.

(21) Appl. No.: 17/894,949

(22) Filed: Aug. 24, 2022

(65) Prior Publication Data

US 2023/0069545 A1     Mar. 2, 2023

Related U.S. Application Data

(60) Provisional application No. 63/237,042, filed on Aug. 25, 2021.

(51) Int. Cl.
| | | |
|---|---|---|
| *A63B 71/06* | (2006.01) | |
| *A63B 22/02* | (2006.01) | |
| *A63B 24/00* | (2006.01) | |

(52) U.S. Cl.
CPC ........ *A63B 71/0622* (2013.01); *A63B 22/025* (2015.10); *A63B 24/0062* (2013.01);
(Continued)

(58) Field of Classification Search
CPC .............. A63B 71/0622; A63B 22/025; A63B 24/0062; A63B 24/0087; A63B 71/0619;
(Continued)

(56) References Cited

U.S. PATENT DOCUMENTS

| | | |
|---|---|---|
| 2009/0227429 A1 | 9/2009 | Baudhuin |
| 2016/0220867 A1 | 8/2016 | Flaherty |

(Continued)

FOREIGN PATENT DOCUMENTS

| | | |
|---|---|---|
| EP | 2633888 | 9/2013 |

OTHER PUBLICATIONS

International Search Report received in counterpart PCT/US2022/041423, mailed Nov. 24, 2022, 5 pages.
(Continued)

*Primary Examiner* — Sundhara M Ganesan
(74) *Attorney, Agent, or Firm* — Klarquist Sparkman, LLP

(57) ABSTRACT

A system includes an exercise machine and a computing device coupled to the exercise machine. The computing device presents a metrics bar within a graphical user interface in an initial state, detects a start of a first workout experience by a user on the exercise machine, retrieve a first set of metrics from stored user preferences data based on a workout experience type, workout type, and exercise machine type of the first workout experience, and displays the first set of metrics in a display area of the metrics bar during the first workout experience. The computing device detects a start of a second workout experience, determines a second set of metrics from the stored user preferences data based on a workout experience type, workout type, and exercise machine type of the second workout experience, and displays the second set of metrics in the metrics bar during the second workout experience.

20 Claims, 24 Drawing Sheets

(52) U.S. Cl.
CPC ...... *A63B 24/0087* (2013.01); *A63B 71/0619* (2013.01); *A63B 2071/065* (2013.01); *A63B 2071/0675* (2013.01)

(58) Field of Classification Search
CPC ...... A63B 2071/065; A63B 2071/0675; G16H 20/30; G16H 40/63; H04W 12/06; G06F 21/31; G06F 2221/2133
See application file for complete search history.

(56) References Cited

U.S. PATENT DOCUMENTS

| | | |
|---|---|---|
| 2017/0326411 A1* | 11/2017 | Watterson .......... A63B 22/0214 |
| 2018/0126248 A1 | 5/2018 | Dion et al. |
| 2020/0009444 A1 | 1/2020 | Putnam |
| 2020/0254311 A1 | 8/2020 | Watterson et al. |
| 2021/0170234 A1* | 6/2021 | Watterson ................ G09B 5/06 |

OTHER PUBLICATIONS

Written Opinion received in counterpart PCT/US2022/041423, mailed Nov. 24, 2022, 6 pages.

* cited by examiner

FIG. 11A

| 00:20 ZONE TIMER | ▬ BURN RATE | ᨊ WORKOUT |
|---|---|---|
| 8:27 TIME | 2.34 MI DISTANCE | 101 CALORIES |
| 45 RPM CADENCE | 25 RESISTANCE | ⚙ |

FIG. 11B

| | ▬ BURN RATE | 25 RESISTANCE | ⚙ |
|---|---|---|---|

FIG. 11C

| 8:27 TIME | 101 CALORIES | 45 RPM CADENCE |
|---|---|---|
| 2.34 MI DISTANCE | 25 RESISTANCE | |
| 107 BPM HEART RATE | | ⚙ |

FIG. 11D

| | 25 RESISTANCE | ⚙ |
|---|---|---|

| 00:20 ZONE TIMER | [icon] BURN RATE | 101 CALORIES | [workout icon] WORKOUT |
|---|---|---|---|
| 8:27 TIME | | | 45 RPM |
| 107 BPM HEART RATE | 25 RESISTANCE | | [gear icon] |

| | | | |
|---|---|---|---|
| | [icon] BURN RATE | 25 RESISTANCE | [gear icon] |

| | | 101 CALORIES | 45 RPM |
|---|---|---|---|
| 8:27 TIME | | | |
| 107 BPM HEART RATE | 25 RESISTANCE | | [gear icon] |

| | | |
|---|---|---|
| | 25 RESISTANCE | [gear icon] |

MODULAR METRICS BAR FOR AN EXERCISE MACHINE

CROSS-REFERENCE TO RELATED APPLICATIONS

This application claims the benefit of U.S. Provisional Application No. 63/237,042, filed Aug. 25, 2021, which is incorporated herein by reference in its entirety.

FIELD

The field generally relates to stationary exercise machines and, more specifically, to user interfaces for exercise machines.

BACKGROUND

Various types of stationary exercise machines (e.g., treadmill, elliptical machines, etc.) exist to aid the user in performing physical exercise. These exercise machines often include consoles that allow the user to control the exercise machine and that display various information related to use of the exercise machine. For example, during a workout session, the console might display metrics related to the workout session, such as settings of the machine and various information calculated based on machine settings and sensors (e.g., caloric burn and heart rate). There continues to be a need for improvements in the user interface experience.

BRIEF DESCRIPTION OF THE DRAWINGS

FIGS. 11A-11D are schematic illustrations of example modular metric bar configurations for a stationary bike.

FIGS. 13A-13D are schematic illustrations of example modular metric bar configurations for a hybrid trainer.

DETAILED DESCRIPTIONS

Example 1—Modular Metrics Bar Overview

An exercise machine (e.g., treadmill, stationary bike, elliptical machine, etc.) can have a console with a display (which can also be referred to as an embedded screen) for user interaction or can communicate with a portable device (e.g., a mobile phone or tablet) having a display (which can also be referred to as a non-embedded screen) for user interaction. The display can include a touch screen. Alternatively, the user can interact with the display using an input device that is communicatively coupled to the console. A machine application that allows interaction with the exercise machine can run on the console or on the portable device. The machine application can provide an application user interface (UI) (e.g., a graphical user interface (GUI)) with UI elements (e.g., graphical user interface elements) linked to various features of the exercise machine. The machine application UI can have a display area for videos and multimedia content.

Figure 9A:
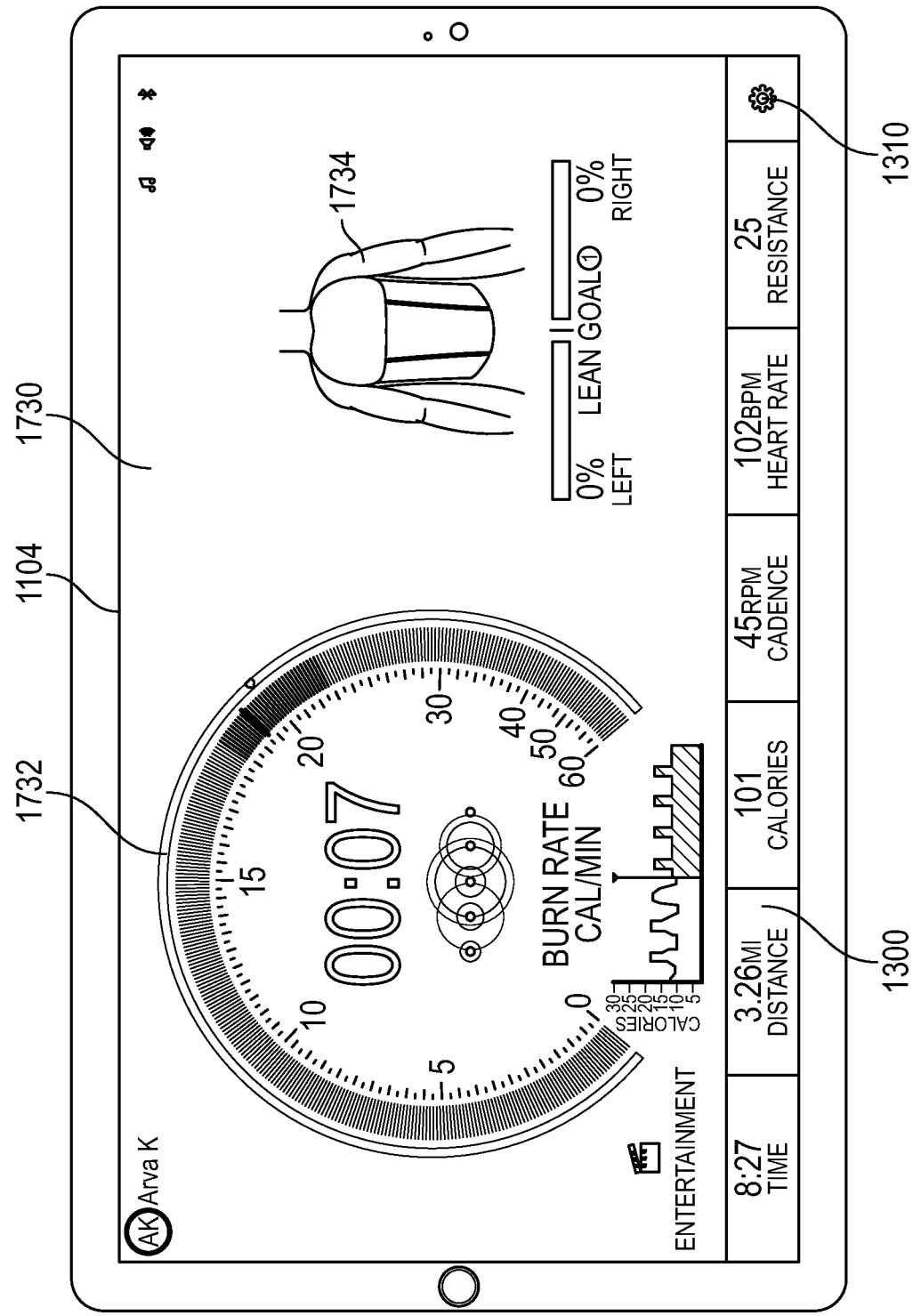
FIG. 9A illustrates an example modular metrics bar anchored relative to a workout experience screen view including a program tachometer in a graphical user interface.

In examples herein, the machine application can provide a modular metrics bar that is responsive to workout states during use of the exercise machine. The modular metrics can be presented within a graphical user interface of the display. The modular metrics bar can allow metrics (e.g., fitness metrics) to be displayed consistently among various screen views (e.g., 2-3 screen views). For example, in FIG. 8A, the modular metrics bar 1300 is at the bottom in the example workout experience screen view 1720 (e.g., "Explore the World and Video" screen view) and displays a set of metrics within the context of the workout experience. In the example workout experience screen view 1730 (e.g., "Program Tach"

screen) in FIG. 9A, the modular metrics bar 1300 is still at the bottom and displays a set of metrics within the context of the workout experience. The modular metrics bar can adapt to multiple workout states (see FIGS. 3A-3C). The metrics displayed on the modular metrics bar can depend on the type of exercise machine, the type of workout, and the type of workout experience.

Figures 4A, 4B:
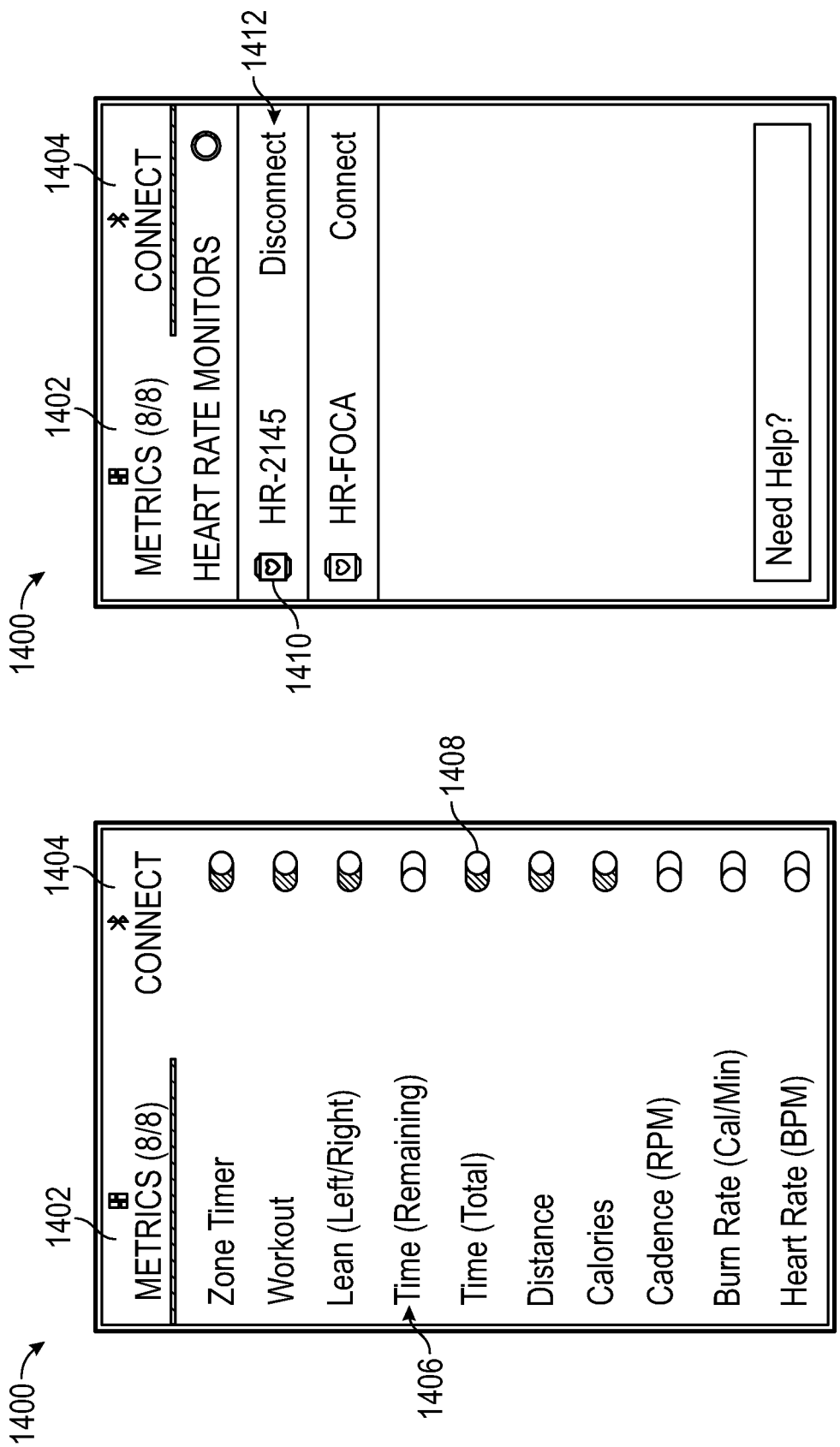
FIGS. 4A-4B are screenshots of different tabs of a metrics bar menu.
Figure 5A:
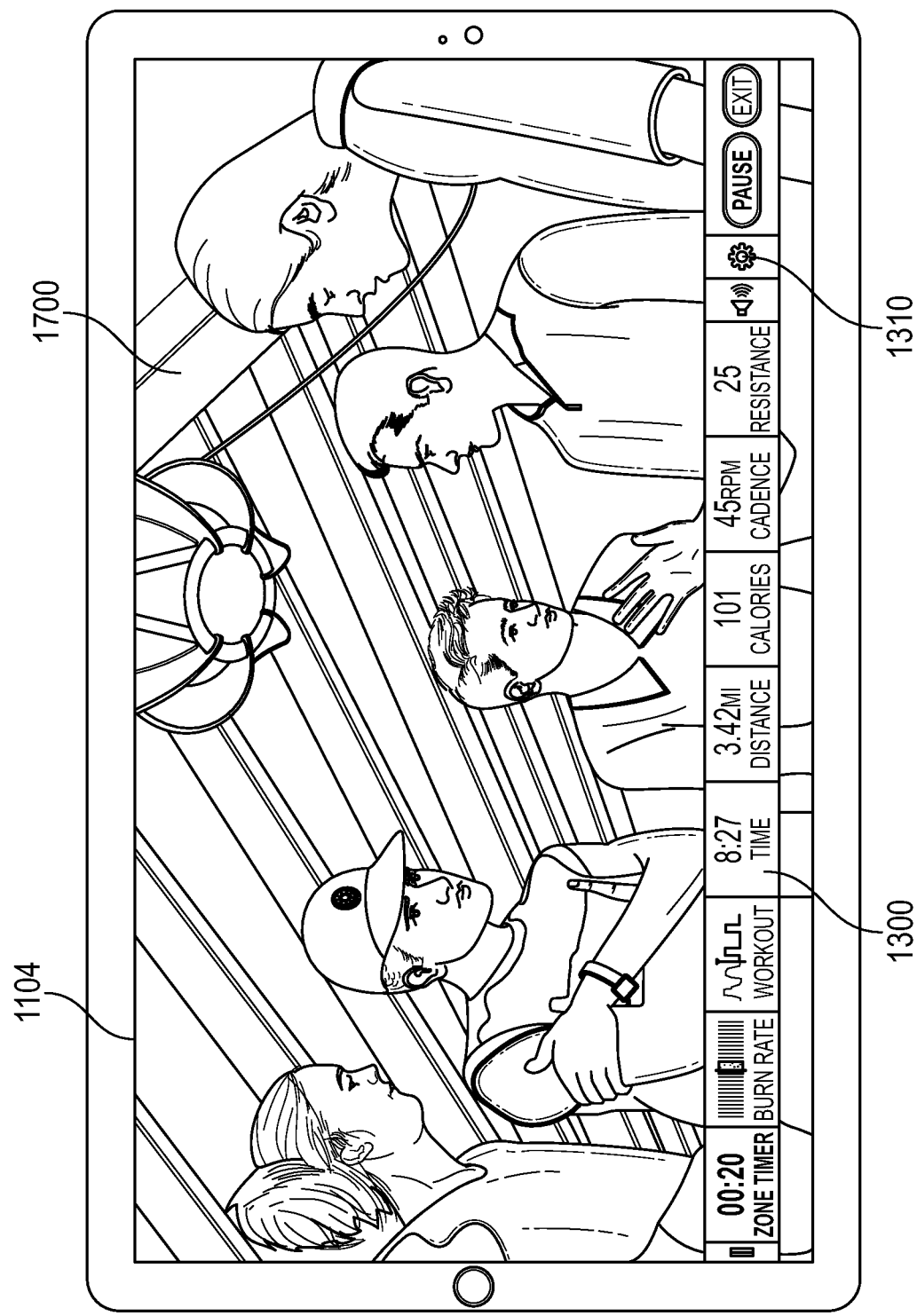
FIG. 5A illustrates an example modular metrics bar floating relative to a workout experience screen view including streaming entertainment in a graphical user interface.
Figure 5B:
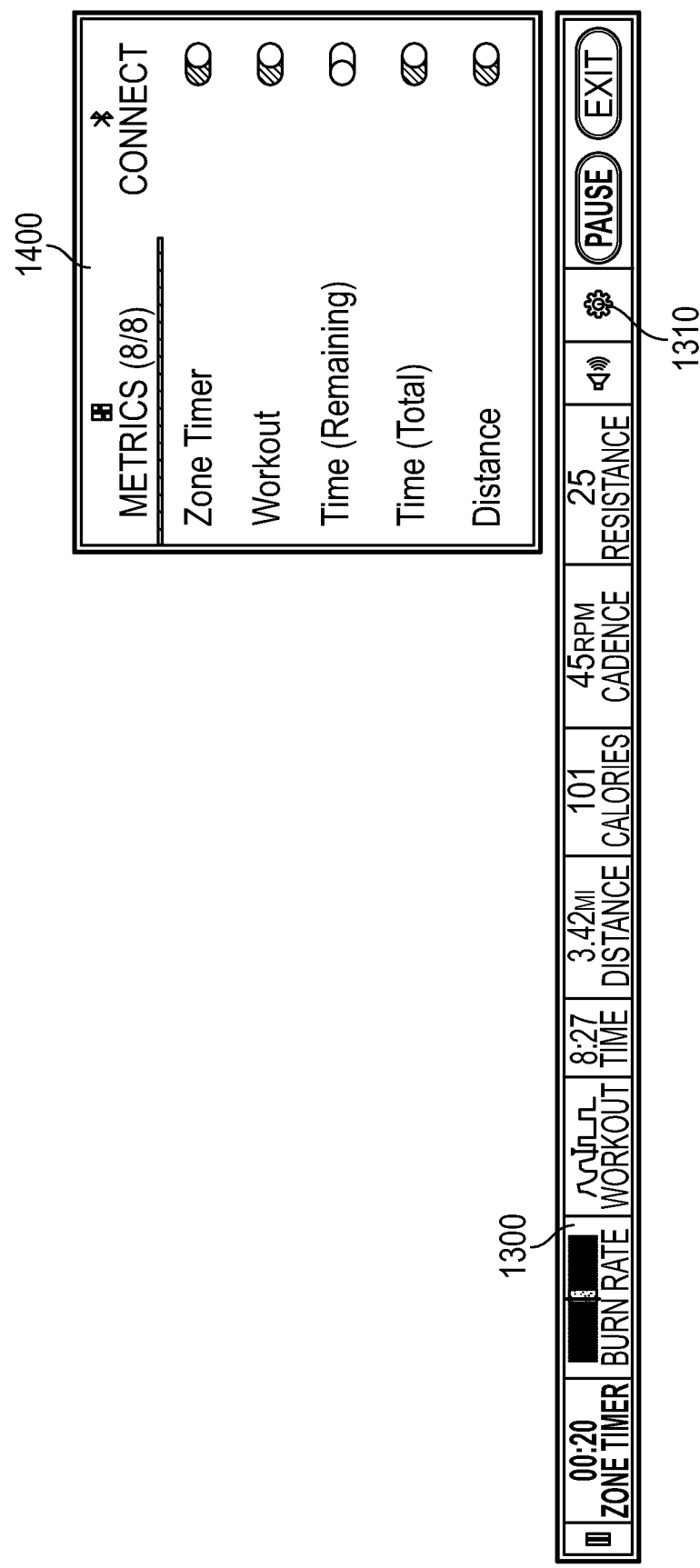
FIG. 5B illustrates an example metrics menu bar corresponding to the floating modular metrics bar shown in FIG. 5A.
Figure 6A:
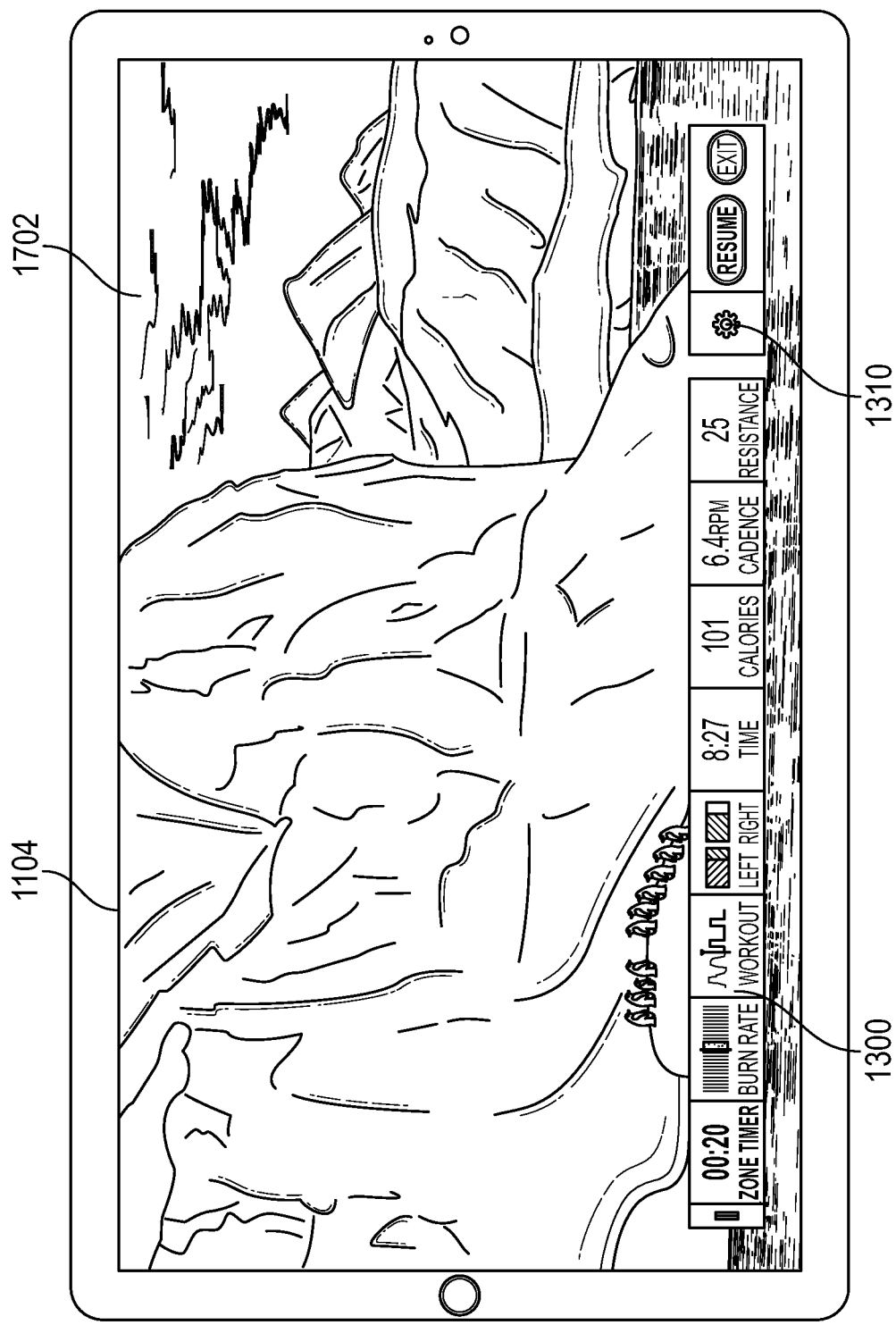
FIG. 6A illustrates an example modular metrics bar floating relative to a workout experience screen view including streaming entertainment in a graphical user interface.
Figure 6B:
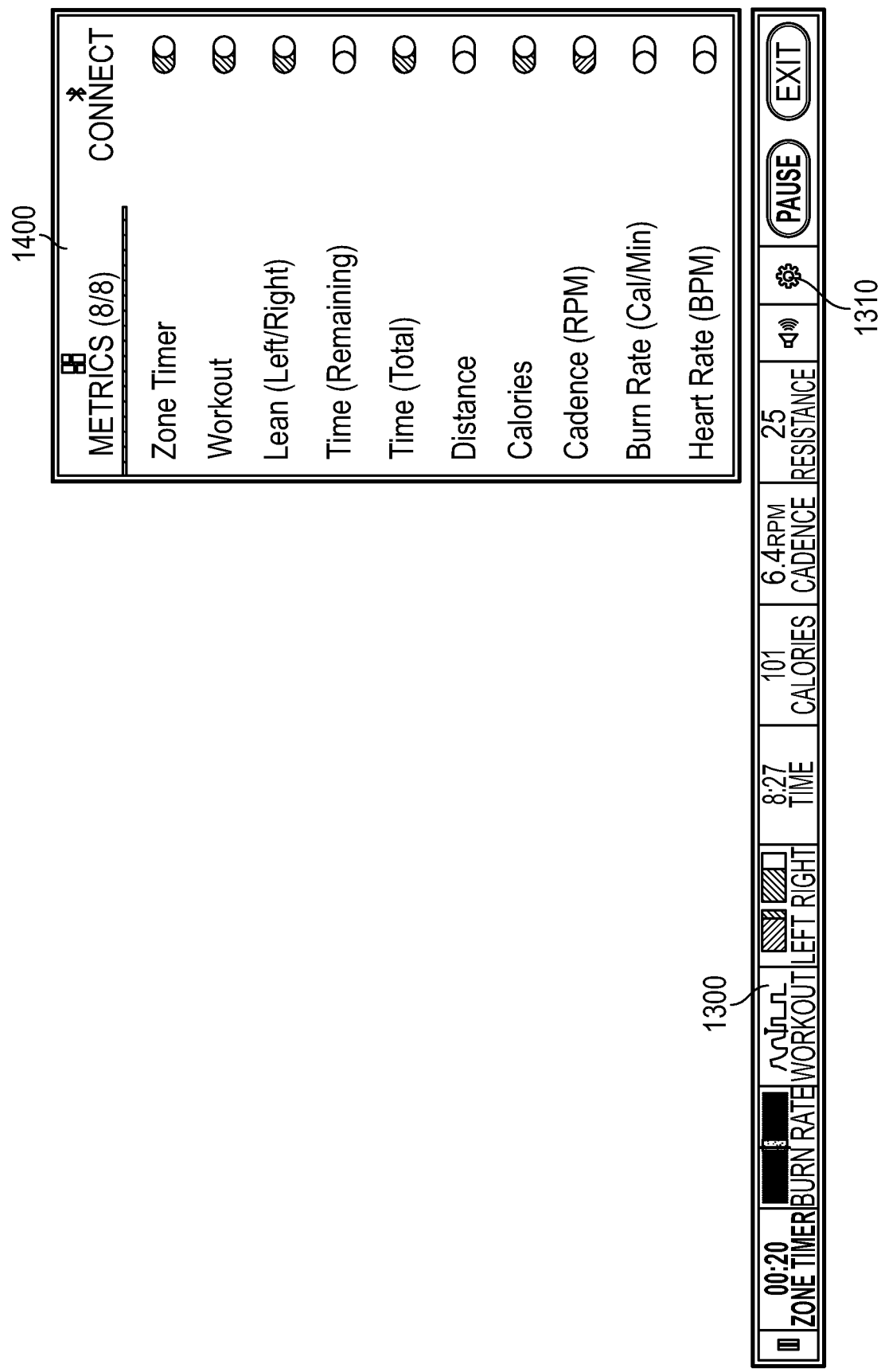
FIG. 6B illustrates an example metrics menu bar corresponding to the floating modular metrics bar shown in FIG. 6A.
Figure 7A:
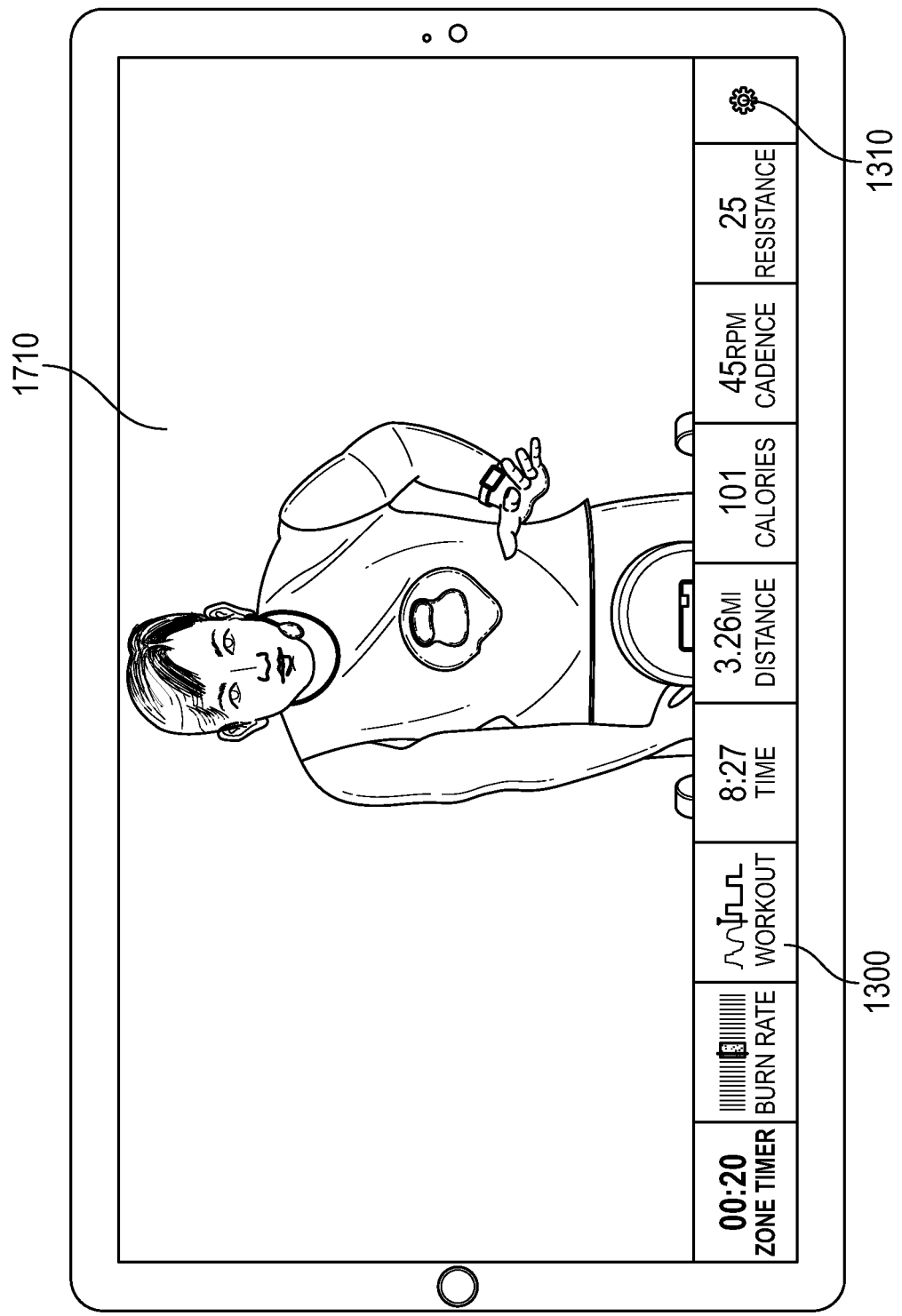
FIG. 7A illustrates an example modular metrics bar anchored relative to a workout experience screen view including a training video in a graphical user interface.
Figure 7B:
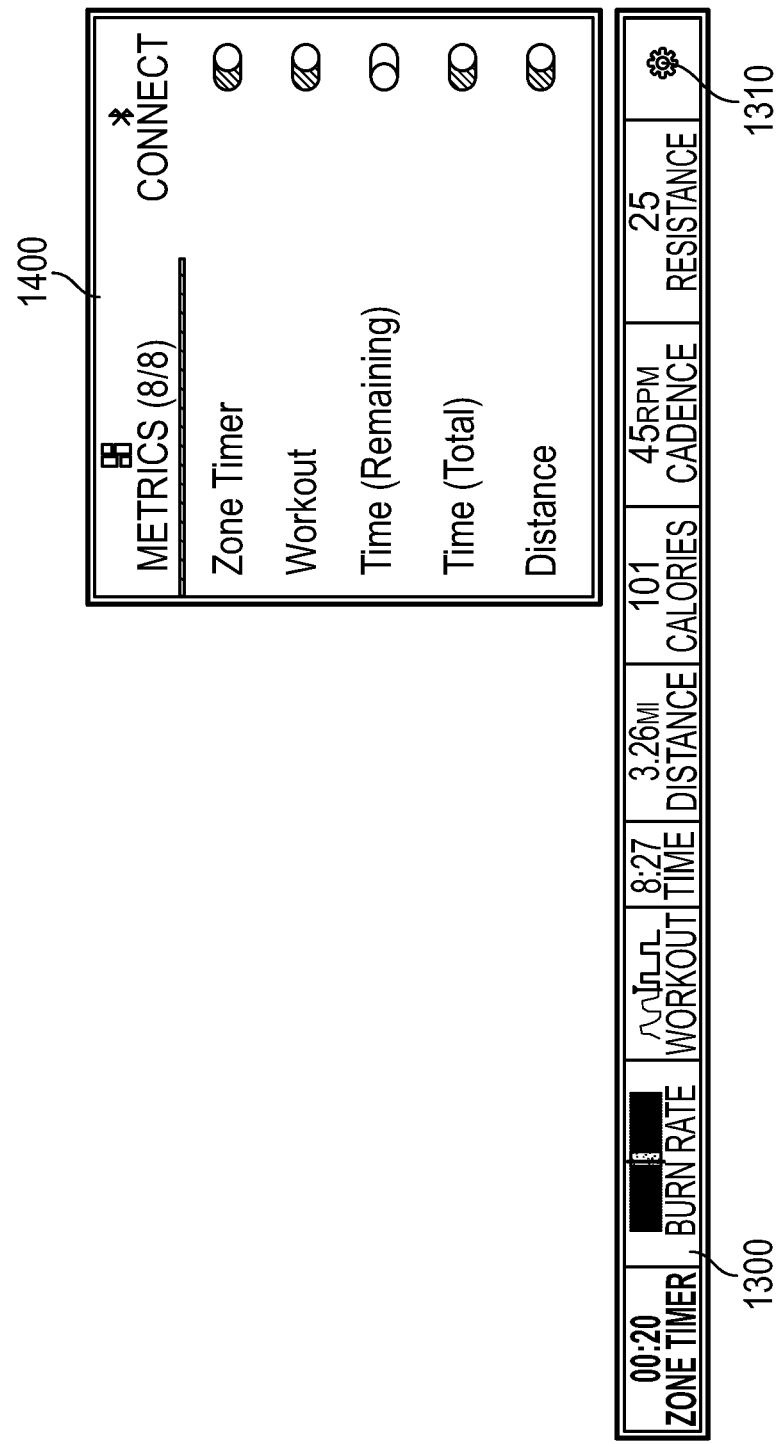
FIG. 7B illustrates an example metrics menu bar corresponding to the anchored modular metrics bar shown in FIG. 7A.
Figure 8A:
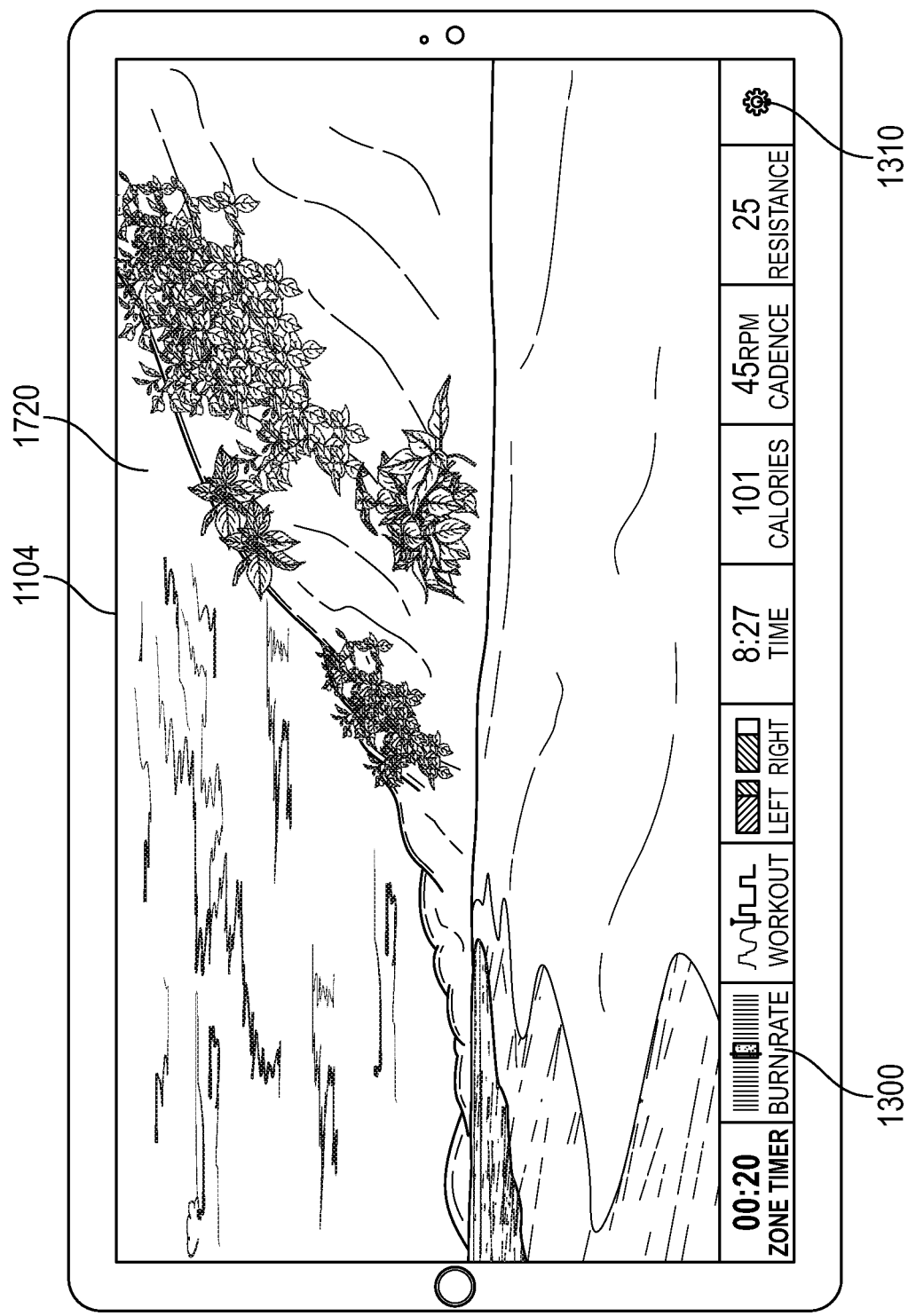
FIG. 8A illustrates an example modular metrics bar anchored relative to a workout experience screen view including an explore the world video in a graphical user interface.

The modular metrics bar can be a floating bar (as illustrated in FIGS. 5A and 6A) or an anchored bar (as illustrated in FIGS. 7A, 8A, and 9A). The floating bar is draggable around a screen view on a display, for example, using handles on the bar, while the anchored bar is fixed relative to the screen view. The modular metrics bar can be configurable through a metrics bar menu (metrics bar menus are shown in FIGS. 4A-6B) accessible from the modular metrics bar (e.g., through a settings button or gear icon in the modular metrics bar). The modular metrics bar can have a profile or shape or layout tailored to the display screen size. For example, the modular metrics bar can have menu items arranged in a single row (as shown in FIGS. 5A-6B) for a larger screen size or in a grid of rows and columns (as shown in FIG. 7B) for a smaller size. The sizing of the modular metrics bar can be dynamic (e.g., display cells can be added to or removed from the modular metrics bar as metrics are added to and removed from the modular metrics bar).

Examples of exercise machines that can use the modular metrics bar are described in, for example, U.S. Pat. No. 10,398,932 and U.S. Patent Publication No. 2021/0197015, which are incorporated herein by reference.

Example 1A—Metrics

A metric is a parameter that can be measured or calculated during use of an exercise machine (e.g., a stationary bike, treadmill, hybrid trainer, elliptical machine, leaning exercise bike, etc.). An exercise machine can have an associated set of metrics that can be measured or calculated when a user uses the machine. A user can choose metrics from the library of metrics to display in a modular metrics bar presented on a display associated with an exercise machine. In some examples, a workout type can have a minimum required set of metrics that is automatically displayed in the modular metrics bar when a user starts a workout experience having the workout type. The user can choose to display additional metrics in the modular metrics bar during the workout experience. Any changes the user makes to the modular metrics bar can be saved and automatically loaded the next time the user engages in the same workout experience.

For illustration purposes, Table 1 below shows examples of metrics that can be included in the library of metrics for four different types of exercise machines.

TABLE 1

| Metrics | Description | Stationary Bike | Leaning Bike | Treadmill | Elliptical Machine |
| --- | --- | --- | --- | --- | --- |
| Time-Remaining | Time remaining in the workout, counting down to zero | Yes | Yes | Yes | Yes |
| Time-Total | Total time of the workout, counting up to total workout duration | Yes | Yes | Yes | Yes |
| Zone Timer | Time remaining in the current zone section within the workout profile | Yes | Yes | Yes | Yes |
| Distance | Distance traveled during workout | Yes | Yes | Yes | No |
| Calories | Number of calories burned during workout | Yes | Yes | Yes | Yes |
| Burn Rate Tach | Tachometer for the rate of calories burned during the workout | Yes | Yes | Yes | Yes |
| Heart Rate | Rate of user heart beat | Yes | Yes | Yes | Yes |
| Cadence | Revolutions per minute (RPM) | Yes | Yes | No | No |
| Burn Rate | Number value for the rate of calories burned | Yes | Yes | Yes | Yes |
| RPM | Revolutions per minute | No | No | No | Yes |
| Resistance | Value of product resistance knob/dial/button | Yes | Yes | No | Yes |
| Leaning (Left/Right) | Amount of total cumulative lean (left or right) based on total workout time | No | Yes | No | No |
| Incline | Amount of incline or decline for treadmill deck | No | No | Yes | Yes |
| Speed | Distance traveled over time | No | No | Yes | No |
| Pace | Current pace | No | No | Yes | No |
| Workout | Workout progress | Yes | Yes | Yes | Yes |

Example 2—System Implementing Modular Metrics Bar

Figure 1:
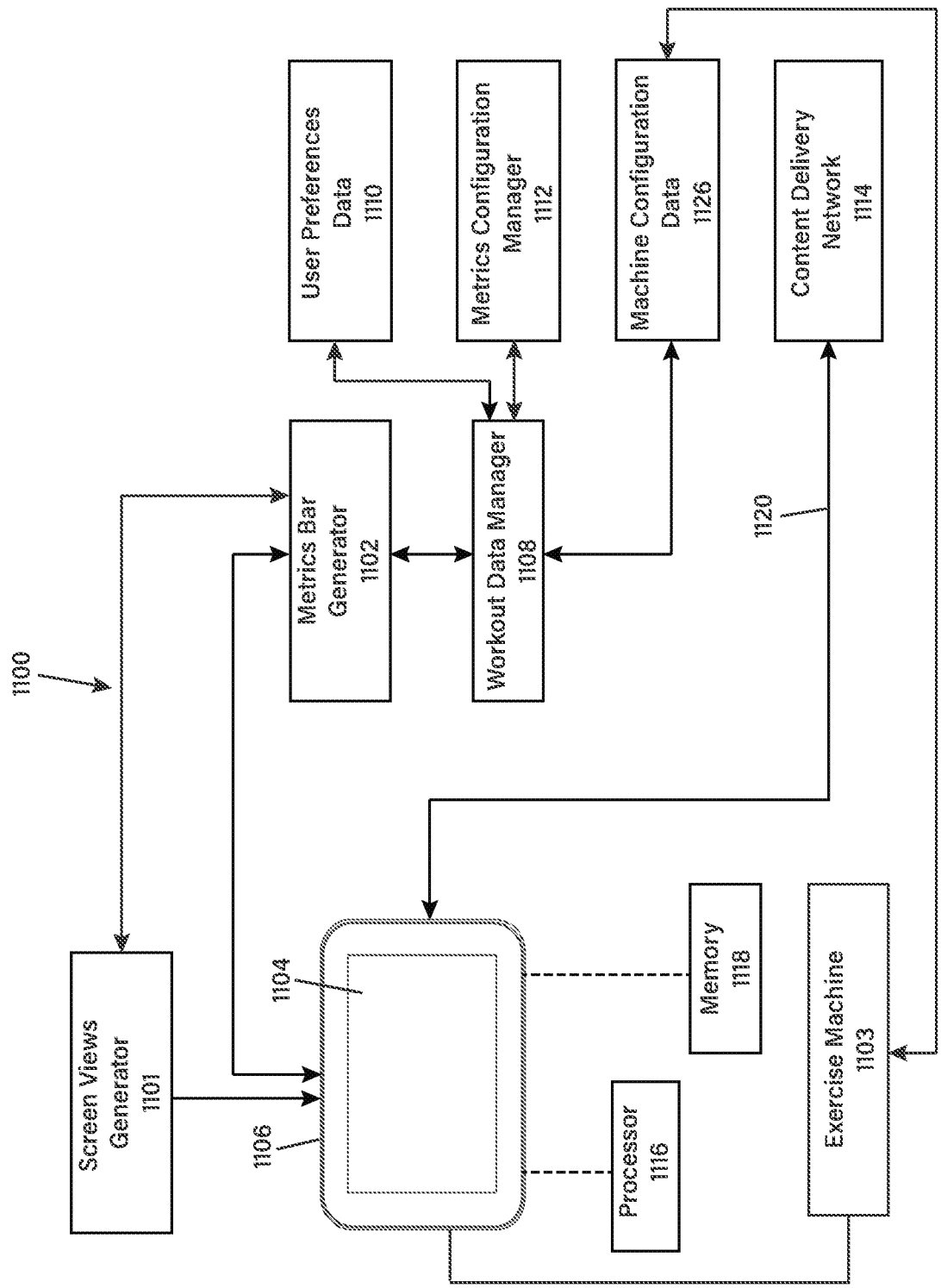
FIG. 1 is a block diagram of a system implementing modular metrics bar, according to one example.

FIG. 1 illustrates an example system 1100 implementing a modular metrics bar. In the example, the system 1100 can include a screen views generator 1101 that generates one or more screen views (e.g., home screen view, workout menu screen view, and workout experience screen view) and presents the screen views within a graphical user interface of a display 1104 of a computing device 1106 during various states of user interaction with an exercise machine 1103 that is associated with the computing device 1106. The system

1100 includes a metrics bar generator 1102 that generates a modular metrics bar and presents the modular metric bar within the graphical user interface of the display 1104. The modular metrics bar is separate from the one or more screens generated by the screen views generator 1101 and presented on the display 1104. The metrics bar generator 1102 can be a component of the screen views generator 1101 in some examples (or vice versa). The metrics bar generator 1102 can detect user interaction with the modular metrics bar presented on the display 1104.

The system 1100 can include a workout data manager 1108 that can communicate with the metrics bar generator 1102. The workout data manager 1108 determines which modular metrics bar the metrics bar generator 1102 should generate and present on the display 1104. For example, the workout data manager 1108 can determine which modular metrics bar to generate based on a workout experience profile that can include the type of exercise machine 1103, the type of workout experience selected by the user on the exercise machine 1103, and the type of workout associated with the selected workout experience. The workout data manager 1108 can receive information about user interaction with the modular metrics bar on the display 1104 from the metrics bar generator 1102. For example, when a user selects a settings button to show a metrics menu, the workout data manager 1108 can be notified of the selection.

The system 1100 can include a metrics configuration manager 1112 that determines which metrics to show on a modular metrics bar for a particular workout state. The metrics configuration manager 1112 can provide metrics to the workout data manager 1108. The metrics configuration manager 1112 can communicate with the exercise machine 1103 (or sensors on the exercise machine) to receive metrics data that can be used in generating the metrics for the modular metrics bar.

The system 1100 can include user preferences data 1110, which can include a record of user preferences related to the modular metrics bar along with other information. For example, the user preferences can indicate which set of metrics should be displayed in a modular metrics bar for a particular workout experience profile. The record of user preferences can be stored in the user preferences data 1110 in association with a user identifier.

The screen views generator 1101, metrics bar generator 1102, workout data manager 1108, metrics configuration manager 1112, and user preferences data 1110 can be part of a machine application running on the computing device 1106 and can be stored on the computing device 1106. The computing device 1106 can be a console embedded in (or attached to) the exercise machine 1103 or can be a portable device (e.g., a phone or tablet) that can communicate with the exercise machine 1103 (e.g., over a Bluetooth connection). The computing device 1106 includes a processor 1116 and memory 1118 to execute instructions of the machine application. The machine application can present a user interface (e.g., a GUI) on the display 1104 that allows user interaction with the exercise machine 1103.

The computing device 1106 can include features to communicate with a content delivery network (CDN) 1114 over a communication link 1120. The computing device 1106 can include additional features to allow the user to consume multimedia content (e.g., audio and video content) as well as receive information from sensors (e.g., heart rate sensor) on the exercise machine.

The system 1100 can include machine configuration data 1126 storing configuration information for the exercise machine (such as the exercise machine type). The machine configuration data 1126 can be stored on a server, which can be in a cloud, for example. The computing device 1106 can communicate with the server over a communication link.

Example 3—Example Method Implementing Modular Metrics Bar Before Workout

Figure 15:
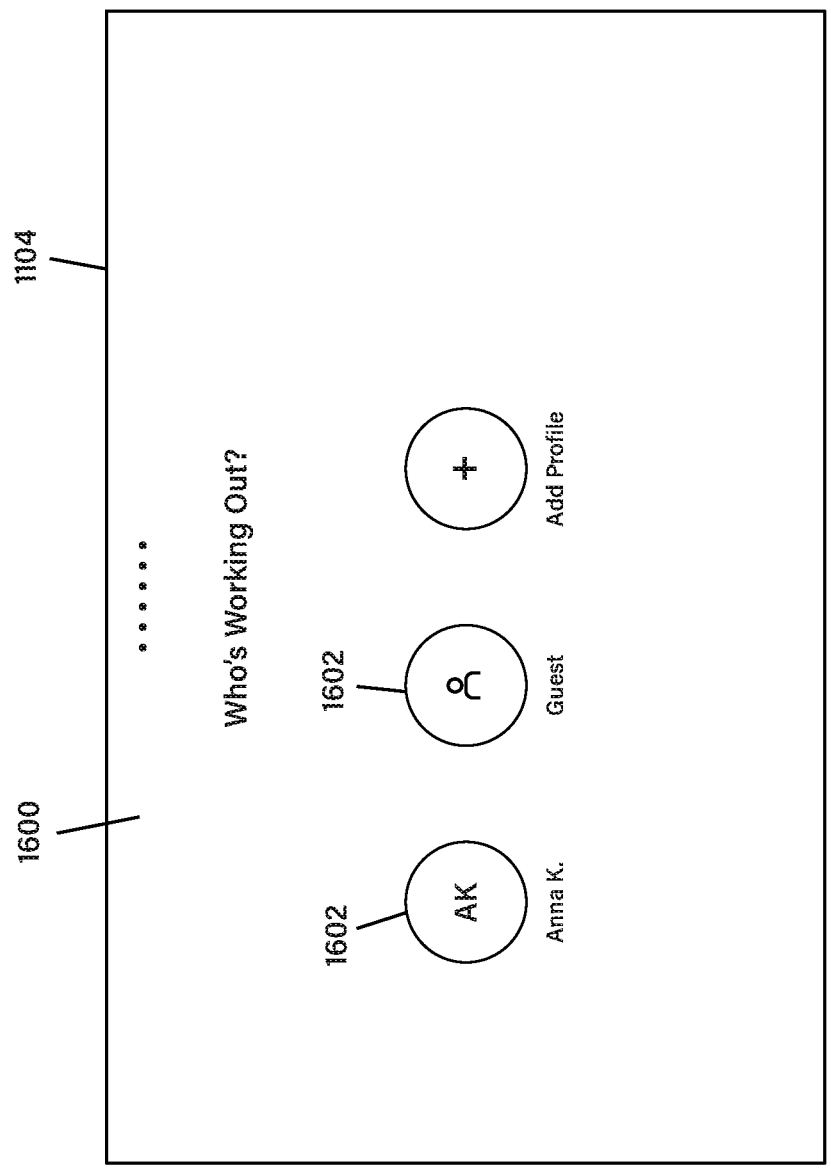
FIG. 15 is a schematic illustration of an example home screen view within a graphical user interface of a display.

When a user starts the exercise machine or wakes up the display 1104 (see Example 2), a home screen view of the machine application UI (or GUI) can be presented on the display 1104. FIG. 15 shows an example of a home screen view 1600 that can be presented on the display 1104. The home screen view 1600 can include a set of user profiles 1602 registered with the exercise machine. Each user profile 1602 can have an associated user identifier and user preferences data. The user can select an appropriate one of the user profiles 1602 to begin using the exercise machine.

Figure 16:
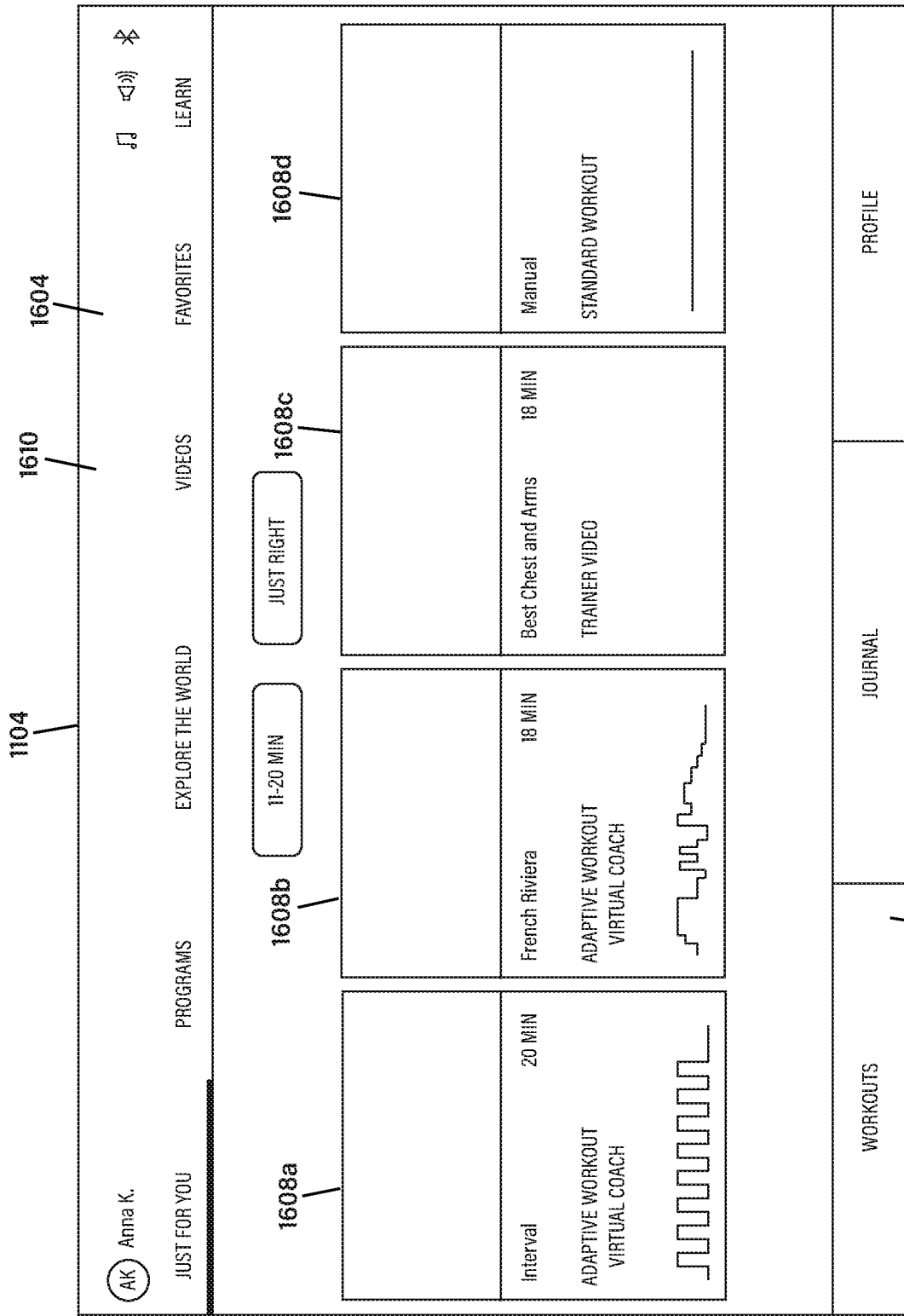
FIG. 16 is a schematic illustration of an example workout menu screen view within a graphical user interface of a display.

In response to selecting a user profile 1602, a workout menu screen view can be presented on the display 1104. FIG. 16 shows an example of a workout menu screen view 1604 on the display 1104. The workout menu screen 1604 can include a set of workout options 1608a-1608d. The workout menu screen 1604 can have a top menu bar 1610 and a bottom menu bar 1612 with access to additional workout options and other features of the machine application. The configuration of the workout menu screen view 1604 and workout options available through the workout menu screen view 1604 can depend on the type of exercise machine. The user can select an appropriate workout from the workout menu screen view 1604 or create and select a custom workout. The selected workout can include a workout type and workout experience.

Figure 17:
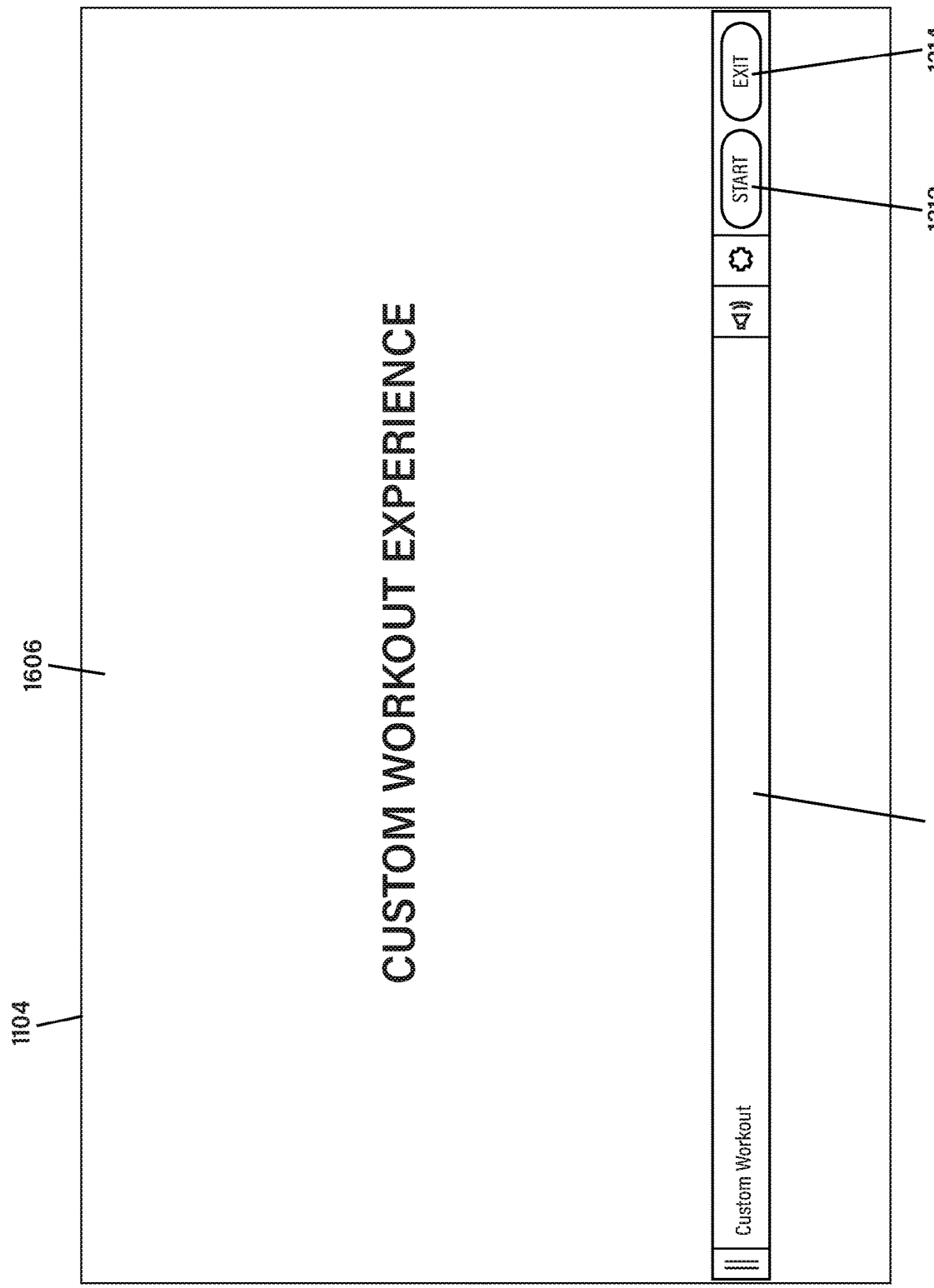
FIG. 17 is a schematic illustration of an example workout experience screen view within a graphical user interface of a display.

After the user selects the workout from the workout menu screen view 1604, a workout experience screen view corresponding to the selected workout can be presented on the display 1104. FIG. 17 shows an example workout experience screen view 1606 on the display 1104. The workout experience screen view 1606 can present a particular workout experience (e.g., streaming entertainment, fitness training video, explore the world simulation, etc.) using any combination of multimedia content, videos, images, text, etc. In some examples, a modular metrics bar 1300 can be presented on the display 1104 contemporaneously with the workout experience screen view 1606. For example, after presenting the workout experience screen view 1606 by the screen views generator 1101 (see Example 2), the metrics bar generator 1102 (see Example 2) can be notified to present the modular metrics bar 1300. In some examples, the modular metrics bar 1300 can be floating relative to the work experience screen view 1606 or anchored relative to the workout experience screen view 1606 (e.g., anchored to any of the edges of the GUI of the display). In some examples, prior to starting the workout, the modular metrics bar 1300 can be in an initial state without a set of metrics. The relevant metrics can be added to the modular metrics bar 1300 after the user starts the workout (see Example 4). The modular metrics bar 1300 can include a first button 1312 (e.g., "START" button) to start the workout and a second button 1314 (e.g., "EXIT" button) to end the workout (see Examples 6-8).

Example 4—Example Method Implementing Modular Metrics Bar at Start of Workout

Figure 2:
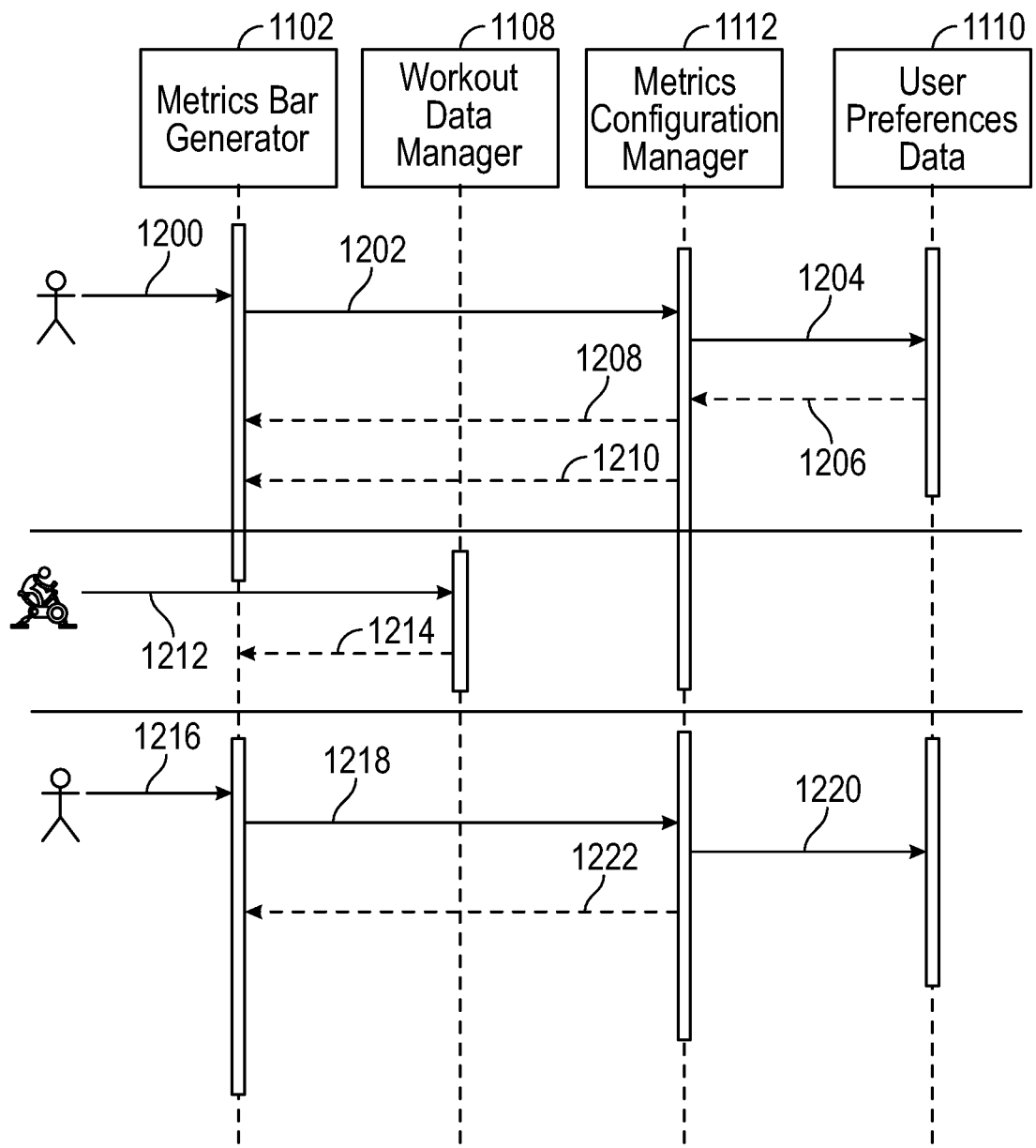
FIG. 2 is a sequence diagram illustrating display of modular metrics bar at the start of and during a workout.

FIG. 2 is a sequence diagram illustrating presentation of metrics on a modular metrics bar during a workout. Prior to the start of the workout by a user, the modular metrics bar can be presented within a GUI of the display in an initial state without a set of metrics (see Examples 3 and 6). The modular metrics bar can be presented floating on or anchored relative to a workout experience screen view (see Example 3) corresponding to a workout experience selected by the user (a workout experience can be, for example, streaming entertainment, simulation video, fitness training video, etc.). As the workout progresses, metrics can be added to or removed from the modular metrics bar to enhance the user workout experience.

In FIG. 2, after the user starts a workout, the metrics bar generator 1102 detects 1200 that the user has started the workout and sends 1202 a request to the metrics configuration manager 1112 for a set of metrics to display to the user. The metrics bar generator 1102 can detect that the user has started a workout, for example, by monitoring outputs from one or more sensors of the exercise machine, such as accelerometers that measure speed of a movable element of the exercise machine. In another example, the user can start the workout by selecting a button (e.g., a "START" button) on the modular metrics bar. The metrics bar generator 1102 can determine that the workout has started by the user interaction with the modular metrics bar.

The request 1200 sent by the metrics bar generator 1102 to the metrics configuration manager 1112 can include the type of workout (e.g., running, walking, climb, interval training, etc., depending on the type of exercise machine), the type of exercise machine (e.g., treadmill, stationary bike, elliptical machine, etc.), the type of workout experience that is currently active (e.g., streaming entertainment, fitness training video, video simulations, etc.), and optionally other information (e.g., identifier of the current user). In some examples, the metrics bar generator 1102 can interact with the metrics configuration manager 1112 through the workout data manager 1108. In response to receiving the request from the metrics bar generator 1102 (or from the workout data manager 1108), the metrics configuration manager 1112 requests 1204 the user preferences data 1110. The request for the user preferences data 1110 can include a user identifier associated with the user profile (see Example 3). In some examples, the user identifier can be obtained from the request 1200 for metrics.

The metrics configuration manager 1112 receives 1206 the user preferences data 1110 and determines if the user has saved metrics for the current workout type, exercise machine type, and workout experience type. If the user has saved metrics, the metrics configuration manager 1112 sends 1208 the user saved metrics to the metrics bar generator 1102, which then updates the modular metrics bar on the display with the user saved metrics. If the user does not have saved metrics, the metrics configuration manager 1112 sends 1210 default metrics for the workout type to the metrics bar generator 1102, which then adds the default metrics to the display area of the modular metrics bar. The metrics bar generator 1102 can additionally send a request to the metrics configuration manager 1112 to save the metrics displayed on the modular metrics bar in the user preferences data 1110 in association with identifiers for the current workout type, workout experience type, and exercise machine type.

Example 5—Example Method Implementing Modular Metrics Bar During Workout

Referring to FIG. 2, during the workout, the workout data manager 1108 receives 1212 workout events and data from the exercise machine and devices on the exercise machine (such as sensors). The workout data manager 1108 sends 1214 the updated metrics to the metrics bar generator 1102, which then updates the modular metrics bar with the updated metrics.

Example 6—Example Method Implementing Modular Metrics Bar with Metric Selection During Workout Referring to FIG. 2, during the workout, the user can select one or more metrics to add to or remove from the modular metrics bar from a metrics bar menu (the menu can be populated with appropriate metrics from a library of metrics as described in Example 1A). In Example 6, during the workout, the metrics bar generator 1102 detects 1216 that a display setting of a given metric has been changed by the user (for example, via the metrics bar menu). The metrics bar generator 1102 sends 1218 a request to the metrics configuration manager 1112 to add or remove the given metric based on the display setting specified by the user. The metrics configuration manager 1112 updates 1220 the user preferences data 1110 with the new display setting. For example, the metrics configuration manager 1112 can obtain the user saved metrics associated with the current workout experience type, workout type, and exercise machine type from the user preferences data 1110 and add or remove the identifier of the given metric from the obtained user saved metrics based on the new display setting. For example, the given metric is added to the user saved metrics if the new display setting is on and removed if the new display setting is off. The updated user saved metrics can be included in the user preferences data 1110. The metrics configuration manager 1112 sends 1222 the updated user saved metrics to the metrics bar generator 1102, which then updates the modular metrics bar on the display with the updated user saved metrics.

Example 7—Example Modular Metrics Bar Before Workout

Figure 3A:
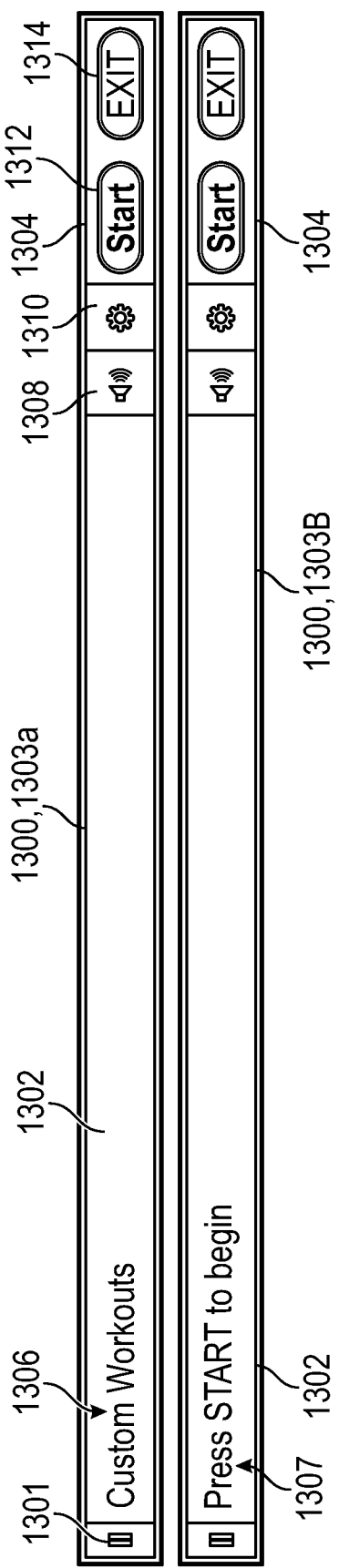
FIGS. 3A-3C show screenshots of a modular metric bar at various states of a workout.

FIG. 3A illustrates a modular metrics bar 1300 that can be displayed on a screen before a workout begins. In the example, the modular metrics bar 1300 includes a display area 1302 for one or more metrics and a controls area 1304. For a floating bar, the modular metrics bar 1300 can include a handle 1301 that can be used to grab the modular metrics bar and drag the modular metrics bar across a screen view. Before the workout begins, the display area 1302 can display the name of the workout 1306 (e.g., "Custom Workouts"), as shown for workout state 1303a of the modular metrics bar 1300. In some examples, every few seconds (e.g., five seconds), a message 1307 (e.g., "Press START to begin") rotates with the name of the workout 1306, as shown for workout state 1303b of the modular metrics bar 1300. The controls area 1304 can include a set of controls or buttons. For example, the controls area 1304 can include a button 1308 for volume control (volume button), a button 1310 to access metrics bar settings (settings button), a button 1312 to start a workout (start button), and a button 1314 to end a workout (exit button).

Example 8—Example Modular Metrics Bar During Workout

Figure 3B:
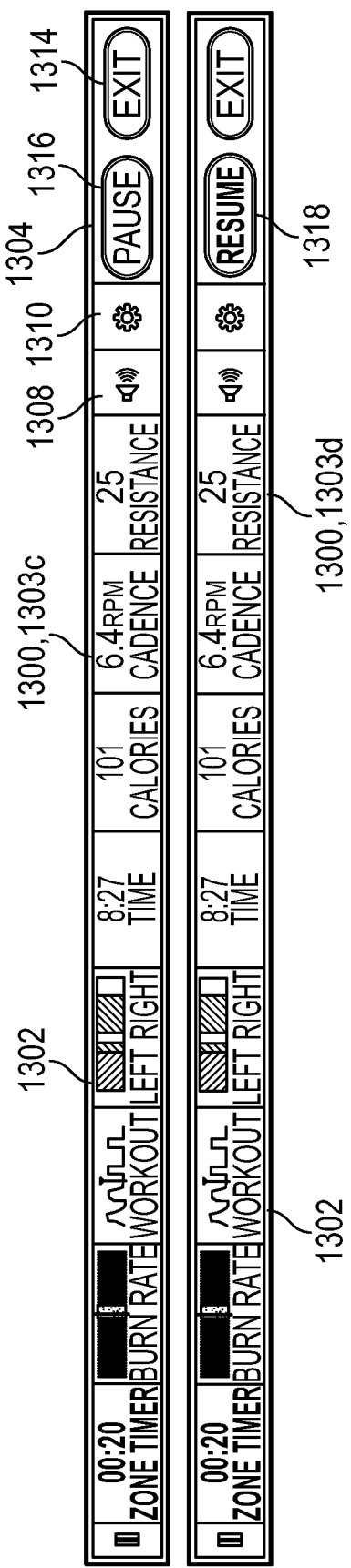

FIG. 3B illustrates the modular metrics bar 1300 of Example 7 during a workout. In the example, the display area 1302 is now populated with a set of metrics. At the start of the workout, the metrics to display in the display area 1302 can be obtained as described in Example 4. As the workout progresses, the metrics in the display area 1302 can be updated according to Example 5. As described in Example 4, user saved metrics or default metrics can be displayed. For illustrative purposes, eight metrics are shown in the display area 1302 (e.g., zone timer, burn rate, workout, lean (left/right), time, calories, cadence, and resistance). In some examples, some of the metrics (e.g., zone timer and burn rate) can be color coded.

The controls or buttons in the controls area 1304 can change based on the workout state. For example, the start button 1312 shown in FIG. 3A has been replaced with a button 1316 to pause the workout (pause button) in workout state 1303c (which can be the state after selecting the start button 1312 in FIG. 3A). The pause button 1316 has been replaced with a button 1318 to resume the workout (resume button) in workout state 1303d (which can be the state after selecting the pause button 1316). If the user selects the pause button 1316, the workout is paused but not ended. The pause button 1316 changes to the resume button 1318 in the paused state. The user can select the resume button 1318 to continue the workout. In the paused state, the metrics displayed in the modular metrics bar 1300 are not updated.

In some examples, the start, pause, resume, and exit buttons can be omitted, and the speed of a movable element of the exercise machine (e.g., pedals, treadmill belt, etc.) can be used to determine whether the workout has started, paused, or resumed. In some examples, the modular metrics bar can be automatically closed when the user exits a workout experience.

Example 9—Example Modular Metrics Bar During Workout

Figure 3C:
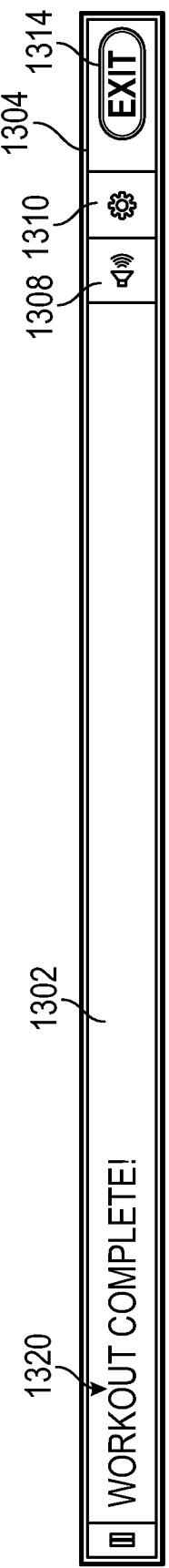

FIG. 3C illustrates the modular metrics bar 1300 of Examples 7 and 8 at the end of a workout. In the example, the metrics have been removed from the display area 1302 and replaced with a message 1320 (e.g., "WORKOUT COMPLETE!). The controls area 1304 includes the volume button 1308, the settings button 1310, and the exit button 1314. None of the start, pause, and resume buttons are shown since the workout has ended. The user can use the exit button 1314 to close the modular metrics bar 1300 and exit the workout. After exiting the workout, the workout menu screen view or the home screen view can be presented on the display.

Example 10—Example Modular Metrics Bar Menu Settings

FIGS. 4A and 4B show an example of a metrics menu bar 1400 that can be accessed via the settings button 1310 (see FIGS. 3A-3C) of the modular metrics bar 1300 (see Examples 7-9). For example, when the user selects the settings button 1310, the metrics menu bar 1400 shown in FIG. 4A can be displayed on the screen. The metrics menu bar 1400 can be a tabbed menu, for example, having a metrics tab 1402 including menu items related to metrics and a connectivity tab 1404 including menu items related to device connections.

The metrics tab 1402 can include a set of metrics 1406 and display setting controls 1408 (e.g., toggle buttons) to indicate whether a particular metric is on or off. In some examples, the set of metrics 1406 can be all possible metrics that can be shown for a particular workout type. In other examples, the set of metrics 1406 can be a subset of all possible metrics that can be shown for a particular workout type (for example, the set of metrics 1406 can exclude required metrics for the exercise machine that cannot be turned off; the required metrics can be based on user experience, for example). The set of metrics 1406 can change based on the particular workout in which the modular metrics bar 1300 is being used when the settings button 1310 is selected. The user preferences data is updated with the changes made in the metrics tab 1402 (see Example 6). According to Example 6, the changes made on the metrics tab 1402 can be detected and can trigger update of the modular metrics bar during a workout.

The connectivity tab 1404 can include a set of devices 1410 (e.g., heart rate monitors) that can make measurements during a workout. The user can indicate which of the devices 1410 to connect to or disconnect from using option controls 1412. The user preferences data can be updated with the changes made in the connectivity tab 1404.

Example 11—Example Implementation of Modular Metrics Bar

In any of the examples herein the modular metrics bar can be implemented as a floating toolbar. The toolbar can be presented across interface modes, resulting in a cross-interface-mode toolbar. For example, one interface mode can comprise presenting video presentations simulating performing a workout routine in geographical locations, while another interface mode comprises video entertainment such as arbitrary streaming video from a service provider (e.g., movies, shows, or the like). The toolbar can be presented across such interface modes.

Example 12—Example Floating Modular Metrics Bar

FIG. 5A shows an example of the modular metrics bar 1300 (Examples 7-9) floating on workout experience screen view 1700 including a streaming entertainment. FIG. 5B shows an example metrics bar menu 1400 that can be displayed within the context of the workout by selecting the settings button 1310. In the example, the workout experience screen view 1700 is on an embedded screen (display 1104) of a stationary bike. The user can adjust the metrics shown in the modular metrics bar 1300 using the metrics bar menu 1400.

FIG. 6A shows an example of the modular metrics bar 1300 (Examples 7-9) floating on a workout experience screen view 1702 including a streaming entertainment. FIG. 6B shows an example metrics bar menu 1400 that can be displayed within the context of the workout by selecting the settings button 1310. In the example, the workout experience screen view 1702 is shown in an embedded screen (display 1104) of a stationary bike (a different type of stationary bike compared to the one in the example of FIGS. 5A-5B). The user can adjust the metrics shown in the modular metrics bar 1300 using the metrics menu bar 1400.

Example 13—Example Anchored Modular Metrics Bar and Menu

FIGS. 7A, 8A, and 9A show examples of the modular metrics bar 1300 in anchored positions adjacent to workout experience screen views. The modular metrics bar 1300 is shown anchored at the bottom edge of the screen views in these examples. In other examples, the modular metrics bar 1300 could be anchored to the top, left, or right edges of the screen views.

In FIG. 7A, the workout experience screen view 1710 includes a training video. In the example, the workout experience screen view 1710 is shown in an embedded screen (display 1104) of a stationary bike. FIG. 7B is an example of the metrics menu bar 1400 that can be displayed within the context of the workout by selecting the settings button 1310. In this example, the minimum required metrics to show in the modular metrics bar 1300 is resistance.

Figure 8B:
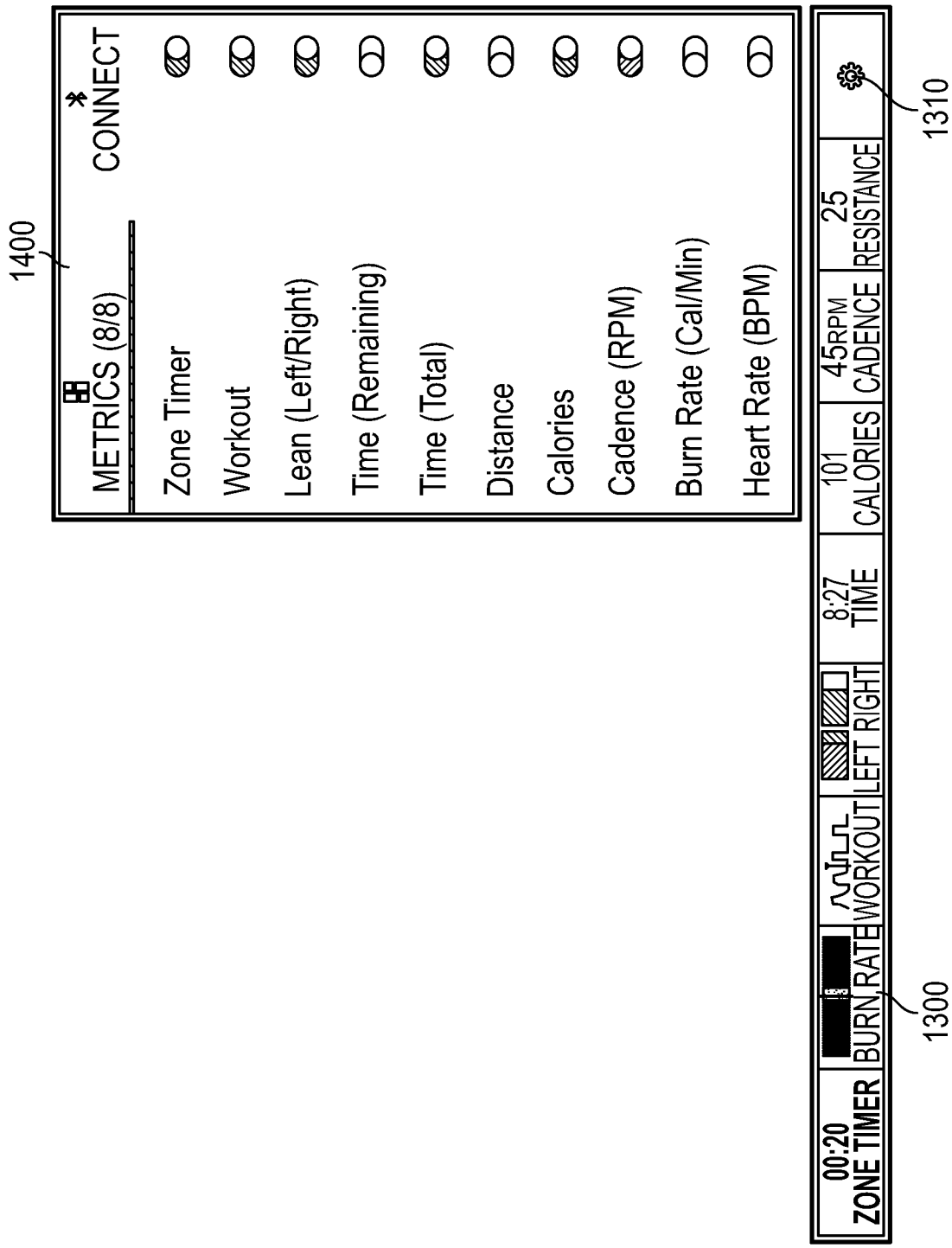
FIG. 8B illustrates an example metrics menu bar corresponding to the anchored modular metrics bar shown in FIG. 8A.

In FIG. 8A, the workout experience screen view 1720 includes an explore the world video. In the example, the workout experience screen view 1720 is shown in an embedded screen (display 1104) of a stationary bike (a different stationary bike from the example of FIGS. 7A-7B). FIG. 8B is an example of the metrics bar 1400 that can be displayed within the context of the workout by selecting the settings button 1310. In this example, the minimum required metrics to show in the modular metrics bar 1300 is resistance.

Figure 9B:
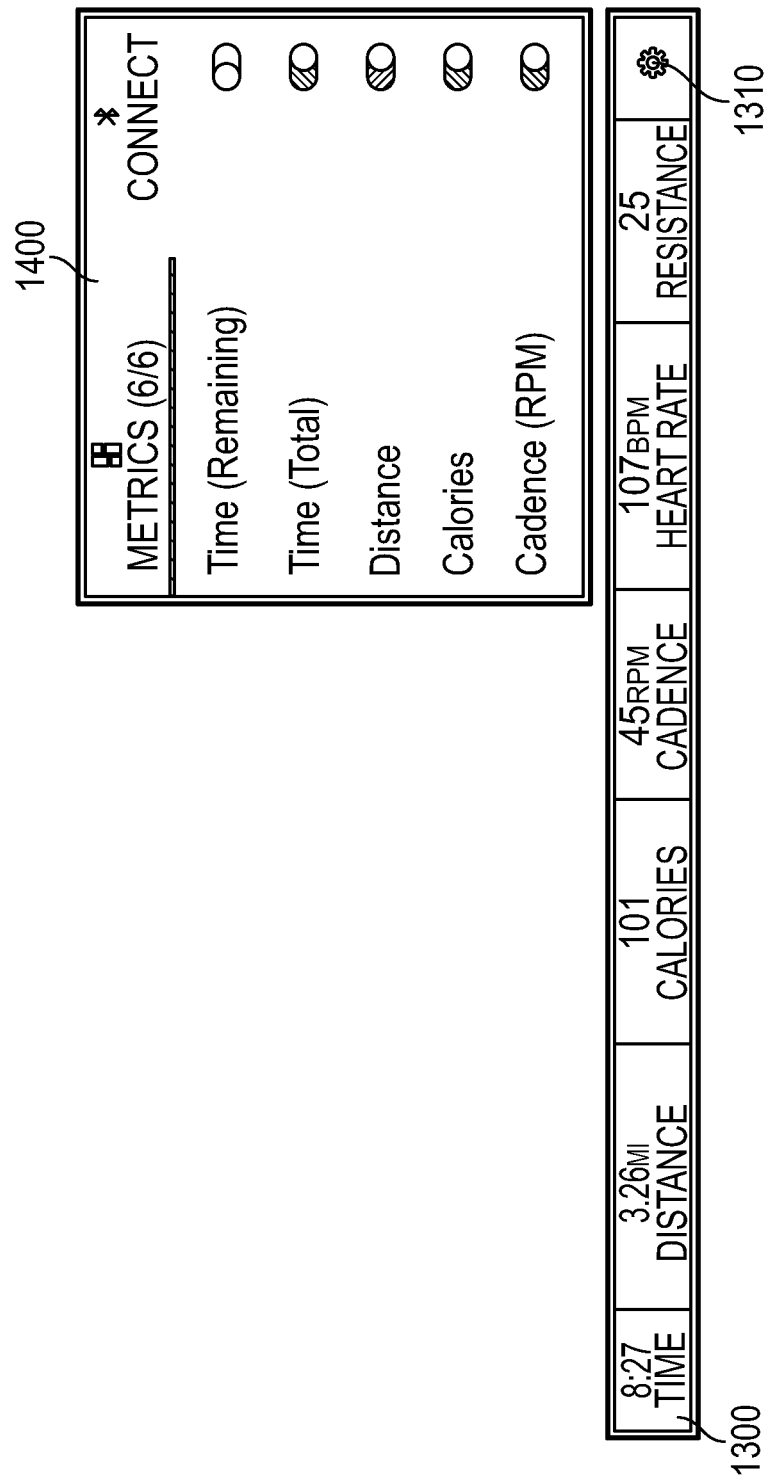
FIG. 9B illustrates an example metrics menu bar corresponding to the anchored modular metrics bar shown in FIG. 9A.

In FIG. 9A, the workout experience screen view 1730 includes a program tachometer 1732 (for example, showing burn rate) and lean goal metric display 1734. In the example, the workout experience screen view 1730 is shown in an embedded screen (display 1104) of a stationary bike (the same stationary bike in the example of FIGS. 7A-7B). Also shown in FIG. 9B is an example of the metrics menu bar 1400 that can be displayed within the context of the workout by selecting the settings button 1310. In this example, the metrics shown in the workout experience screen view 1730 (for example, burn rate and lean metrics) can be optional in the modular metrics bar and metrics menu bar. In this example, the minimum required metrics to show in the modular metrics bar 1300 is resistance.

Example 14—Example Modular Metrics Bar Layout

Figure 10A:
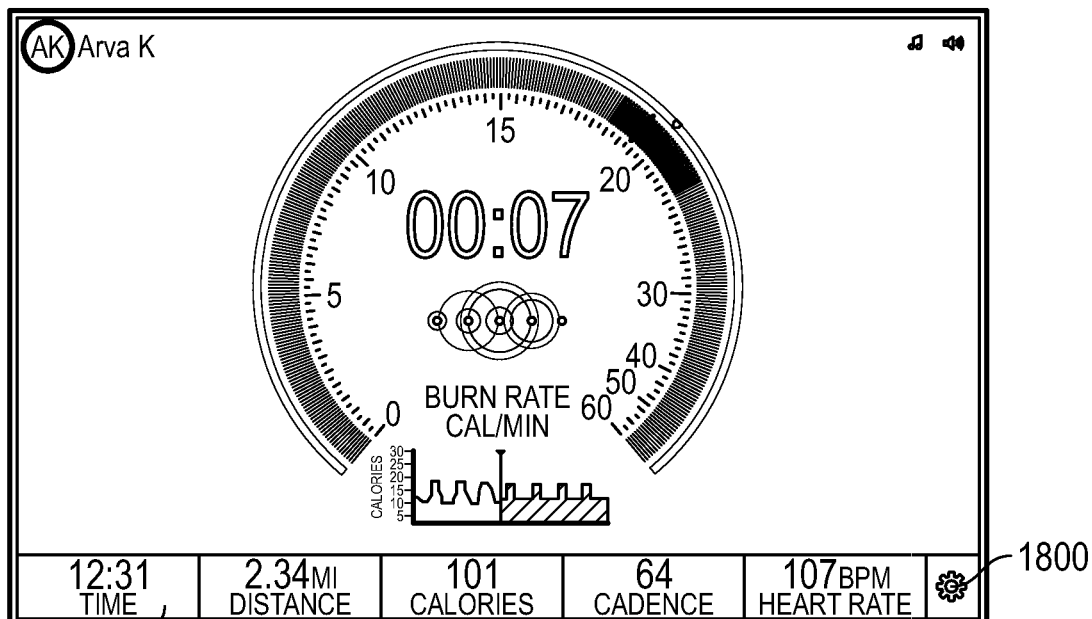
FIG. 10A illustrates an example configuration of a modular metric bar with menu items arranged in a single row.
Figure 10B:
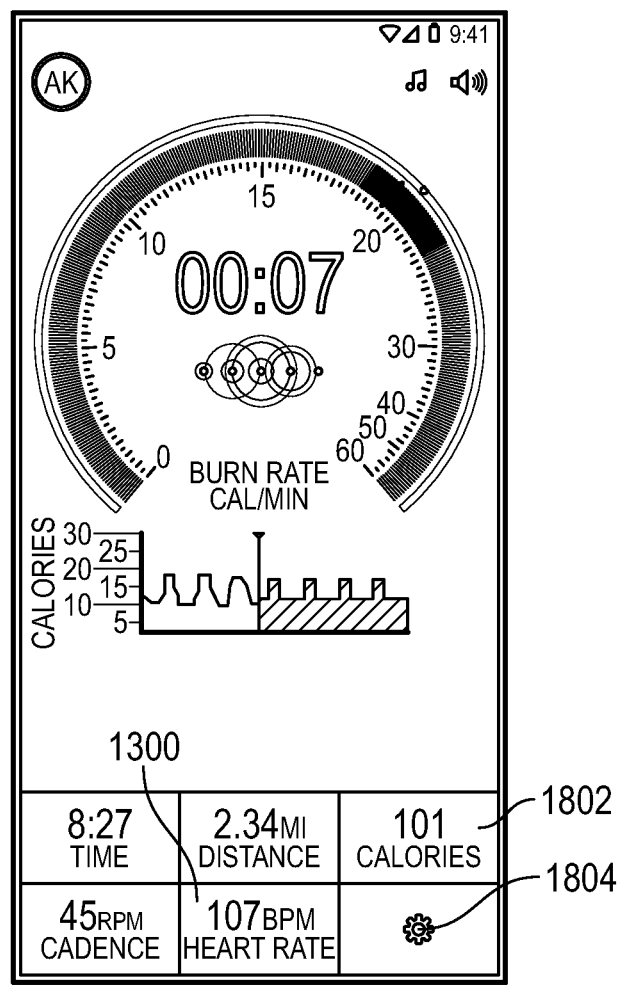
FIG. 10B illustrates an example configuration of a modular metric bar with menu items arranged in two rows.

The metrics and controls items of the modular metrics bar 1300 can be arranged in one or more rows. The arrangement to use can depend on the screen size and orientation of the display 1104. FIG. 10A shows an example where the metrics and controls items of the modular metrics bar 1300 are in a single row 1800. The arrangement in FIG. 10A can be used for large screen sizes or horizontal (or landscape) screen orientation. FIG. 10B shows an example where the same set of modular menu bar items shown in FIG. 10A are now in multiple rows (specifically, two rows 1802, 1804). The arrangement shown in FIG. 10B can be used for small screen sizes or vertical (or portrait) screen orientation. In some examples, the metrics bar generator 1102 can detect the size and orientation of the screen and tailor the arrangement of the menu items of the modular metrics bar 1300 based on the detected size and orientation of the screen.

Example 15—Example Modular Metrics Bar Layout for a Stationary Bike

FIGS. 11A-11D show example arrangements of metrics and controls items for the modular metrics bar 1300 for a stationary bike. FIG. 11B shows the required metrics (e.g., burn rate and resistance) for a workout experience including video or streaming entertainment, and FIG. 11A shows the complete set of metrics (e.g., zone timer, workout progress, time, distance, calories, and cadence) that can be added to the modular metrics bar. FIG. 11D shows the required metrics (e.g., resistance) for a workout experience including a program tachometer (e.g., a burn rate tachometer), and FIG. 11C shows the complete set of metrics (e.g., time, distance, calories, cadence, heart rate, and resistance) that could be added to the modular metrics bar. The modular metrics bar 1300 is shown in a multi-row, anchored format in FIGS. 11A-11D.

Example 16—Example Modular Metrics Bar Layout for a Treadmill

Figure 12A:
FIGS. 12A-12D are schematic illustrations of example modular metric bar configurations for a treadmill.
Figure 12B:
Figure 12C:
Figure 12D:

FIGS. 12A-12D show example arrangements of metrics and controls for the modular metrics bar 1300 for a treadmill. FIG. 12B shows the required metrics (e.g., incline, burn rate, and speed) for a workout experience including video or streaming entertainment, and FIG. 12A shows the complete set of metrics (e.g., incline, zone timer, burn rate, workout progress, time, distance, calories, and speed) that can be added to the modular metrics bar. FIG. 12D shows the required metrics (e.g., incline and speed) for a workout experience including a program tachometer (e.g., a burn rate tachometer), and FIG. 12C shows the complete set of metrics (e.g., incline, time, distance, calories, and speed) that could be added to the modular metrics bar. The modular metrics bar 1300 is shown in a multi-row, anchored format in FIGS. 12A-12D.

Example 17—Example Modular Metrics Bar Layout for a Hybrid Trainer

FIGS. 13A-13D show example arrangements of metrics and controls for the modular metrics bar 1300 for a hybrid trained including a combination of stair stepper and elliptical machine. FIG. 13B shows the required metrics (e.g., burn rate and resistance) for a workout experience including video or streaming entertainment, and FIG. 13A shows the complete set of metrics (e.g., zone timer, burn rate, workout progress, time, calories, speed, heart rate, and resistance) that can be added to the modular metrics bar. FIG. 13D shows the required metrics (e.g., resistance) for a workout experience including a program tachometer (e.g., a burn rate tachometer), and FIG. 13C shows the complete set of metrics (e.g., time, calories, speed, heart rate, and resistance) that could be added to the modular metrics bar. The modular metrics bar 1300 is shown in a multi-row, anchored format in FIGS. 13A-13D.

Example 18—Example Modular Metrics Bar Layout for an Elliptical Machine

Figure 14A:
FIGS. 14A-14D are schematic illustrations of example modular metric bar configurations for an elliptical machine.
Figure 14B:
Figure 14C:
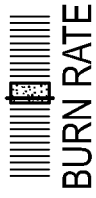
Figure 14D:

FIGS. 14A-14D show example arrangements of metrics and controls for the modular metrics bar 1300 for an elliptical machine. FIG. 14B shows the required metrics (e.g., incline, burn rate, and resistance) for a workout experience including video or streaming entertainment, and FIG. 14A shows the complete set of metrics (e.g., incline, zone timer, burn rate, workout progress, time, calories, heart rate, and resistance) that can be added to the modular metrics bar. FIG. 14D shows the required metrics (e.g., incline and resistance) for a workout experience including a program tachometer (e.g., a burn rate tachometer), and FIG. 14C shows the complete set of metrics (e.g., incline, time, calories, heart rate, and resistance) that could be added to the modular metrics bar. The modular metrics bar 1300 is shown in a multi-row, anchored format in FIGS. 14A-14D.

Example 19—Method of Operating an Exercise Machine with Modular Metrics Bar

Figure 20:
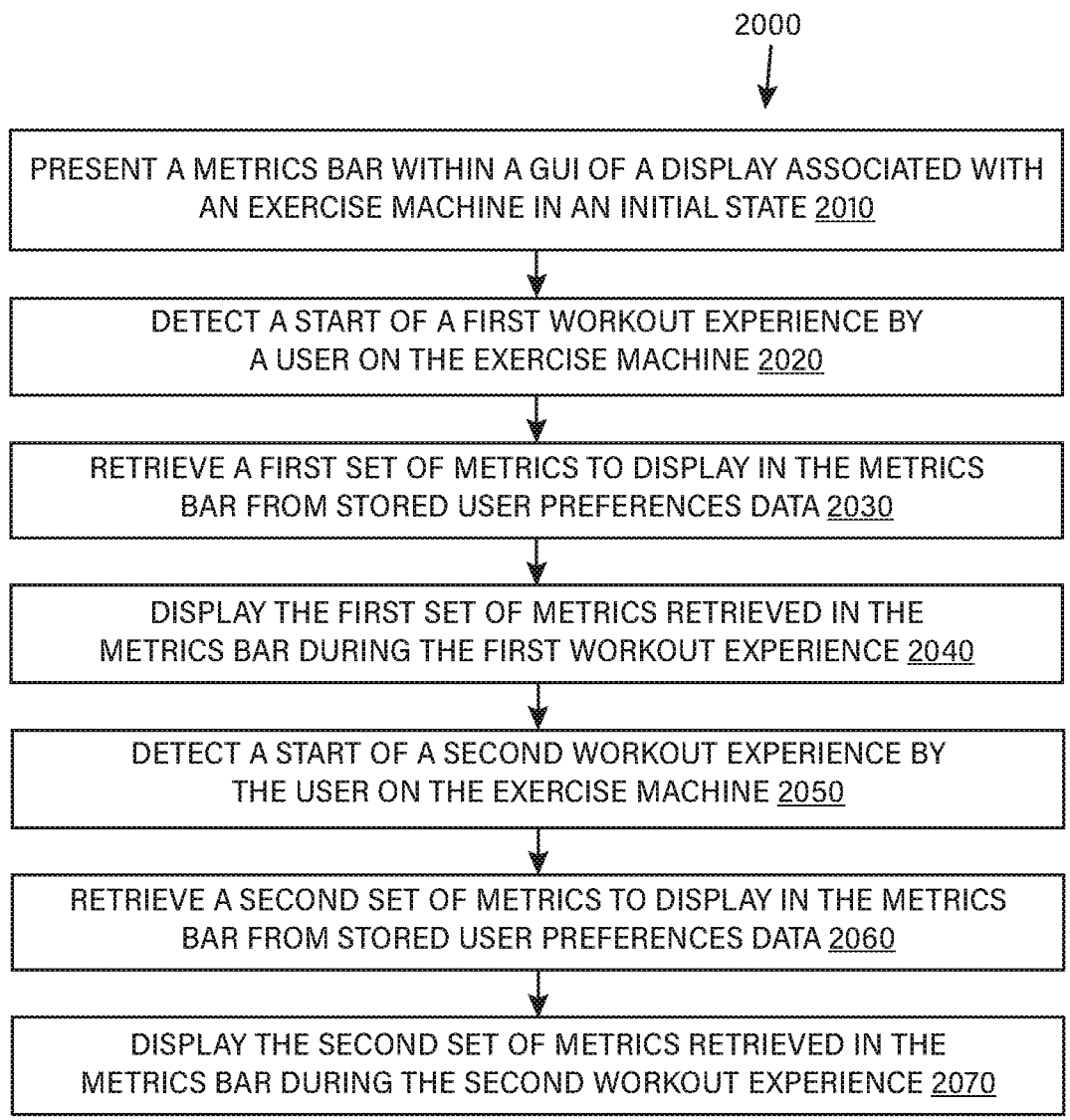
FIG. 20 is a flowchart illustrating a method of operating an exercise machine with a modular metrics bar.

FIG. 20 is a flowchart of an example method 2000 of operating an exercise machine and can be performed, for example, by the system 1100 (see Example 2).

At 2010, the method presents a modular metrics bar within a GUI of a display associated with the exercise machine in an initial state. In one example, the initial state can be a state in which the modular metrics bar does not display any metrics (see FIG. 17). The metrics bar can be presented in the initial state when a new workout experience screen is displayed within the GUI of the display.

At 2020, the method detects the start of a first workout experience by a user on the exercise machine. For example, the method can detect that the user is moving on the exercise machine, or the method can detect that the user has selected a start button from the modular metrics bar.

At 2030, upon detecting the start of the first workout experience, the method retrieves a first set of metrics to display in the modular metrics bar from stored user preferences data associated with the user. The first set of modular metrics retrieved from the stored user preferences data can be associated with a first workout experience profile including a type of the first workout experience (e.g., streaming entertainment, training video, program tachometer, etc.), a type of workout (e.g., running, climbing, walking, interval training, etc.) associated with the first workout experience, and a type of the exercise machine (e.g., stationary bike, treadmill, elliptical machine, leaning bike, etc.).

At 2040, the method displays the first set of metrics retrieved in operation 2030 in the modular metrics bar during the first workout experience. For example, the modular metrics bar can have a display area comprised of cells arranged in one or more rows and one or more columns. The cells can be populated with the first set of metrics.

At 2050, the method detects the start of a second workout experience by the user on the exercise machine. In one example, after conclusion of the first workout experience, the user can select a second workout experience. The selection of the second workout experience can cause a second workout experience screen to be presented within the GUI of the display and return of the metrics bar within the GUI of the display to the initial state. In one example, the method can detect the start of the second workout experience by detecting the presence of the second workout experience screen within the GUI. In another example, the method can detect the start of the second workout experience when a user selects a start button from the metrics bar. In another example, the method can detect the start of the second workout experience by movement of the user on the exercise machine after conclusion of the first workout experience.

At 2060, upon detecting the start of the second workout experience, the method retrieves a second set of metrics to display in the modular metrics bar from the stored user preferences data associated with the user. The second set of metrics retrieved from the stored user preferences data can be associated with a second workout experience profile including a type of the second workout experience (e.g., streaming entertainment, training video, program tachometer, etc.), a type of workout (e.g., running, climbing, walking, interval training, etc.) associated with the second workout experience, and the type of the exercise machine (e.g., stationary bike, treadmill, elliptical machine, leaning bike, etc.).

At 2070, the method displays the second set of metrics retrieved in operation 2060 in the metrics bar during the second workout experience.

EXAMPLE IMPLEMENTATIONS

Although the operations of some of the disclosed methods are described in a particular, sequential order for convenient presentation, such manner of description encompasses rearrangement, unless a particular ordering is required by specific language set forth herein. For example, operations described sequentially can in some cases be rearranged or performed concurrently.

Alternatives

The technologies from any example can be combined with the technologies described in any one or more of the other examples. In view of the many possible embodiments to which the principles of the disclosed technology can be applied, it should be recognized that the illustrated embodiments are examples of the disclosed technology and should not be taken as a limitation on the scope of the disclosed technology. Rather, the scope of the disclosed technology includes what is covered by the scope and spirit of the claims.

Example Computing Systems

Figure 18:
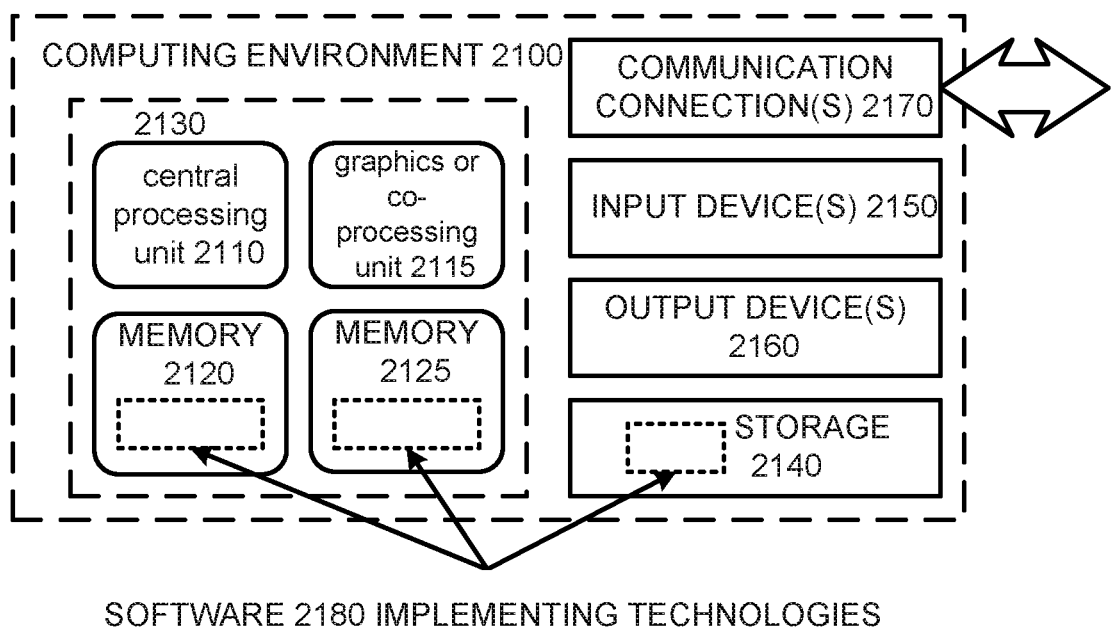
FIG. 18 is a block diagram of an example computing system in which described examples can be implemented.

FIG. 18 depicts an example of a suitable computing system 2100 in which the described innovations can be implemented. The computing system 2100 is not intended to suggest any limitation as to scope of use or functionality of the present disclosure, as the innovations can be implemented in diverse computing systems.

With reference to FIG. 18, the computing system 2100 includes one or more processing units 2110, 2115 and memory 2120, 2125. In FIG. 18, this basic configuration 2130 is included within a dashed line. The processing units 2110, 2115 execute computer-executable instructions, such as for implementing the features described in the examples herein. A processing unit can be a general-purpose central processing unit (CPU), processor in an application-specific integrated circuit (ASIC), or any other type of processor. In a multi-processing system, multiple processing units execute computer-executable instructions to increase processing power. For example, FIG. 18 shows a central processing unit 2110 as well as a graphics processing unit or co-processing unit 2115. The tangible memory 2120, 2125 can be volatile memory (e.g., registers, cache, RAM), non-volatile memory (e.g., ROM, EEPROM, flash memory, etc.), or some combination of the two, accessible by the processing unit(s) 2110, 2115. The memory 2120, 2125 stores software 2180 implementing one or more innovations described herein, in the form of computer-executable instructions suitable for execution by the processing unit(s) 2110, 2115.

A computing system 2100 can have additional features. For example, the computing system 2100 includes storage 2140, one or more input devices 2150, one or more output devices 2160, and one or more communication connections 2170, including input devices, output devices, and communication connections for interacting with a user. An interconnection mechanism (not shown) such as a bus, controller, or network interconnects the components of the computing system 2100. Typically, operating system software (not shown) provides an operating environment for other software executing in the computing system 2100, and coordinates activities of the components of the computing system 2100.

The tangible storage 2140 can be removable or non-removable, and includes magnetic disks, magnetic tapes or cassettes, CD-ROMs, DVDs, or any other medium which can be used to store information in a non-transitory way and which can be accessed within the computing system 2100.

The storage 2140 stores instructions for the software 2180 implementing one or more innovations described herein.

The input device(s) 2150 can be an input device such as a keyboard, mouse, pen, or trackball, a voice input device, a scanning device, touch device (e.g., touchpad, display, or the like) or another device that provides input to the computing system 2100. The output device(s) 2160 can be a display, printer, speaker, CD-writer, or another device that provides output from the computing system 2100.

The communication connection(s) 2170 enable communication over a communication medium to another computing entity. The communication medium conveys information such as computer-executable instructions, audio or video input or output, or other data in a modulated data signal. A modulated data signal is a signal that has one or more of its characteristics set or changed in such a manner as to encode information in the signal. By way of example, and not limitation, communication media can use an electrical, optical, RF, or other carrier.

The innovations can be described in the context of computer-executable instructions, such as those included in program modules, being executed in a computing system on a target real or virtual processor (e.g., which is ultimately executed on one or more hardware processors). Generally, program modules or components include routines, programs, libraries, objects, classes, components, data structures, etc. that perform particular tasks or implement particular abstract data types. The functionality of the program modules can be combined or split between program modules as desired in various embodiments. Computer-executable instructions for program modules can be executed within a local or distributed computing system.

For the sake of presentation, the detailed description uses terms like "determine" and "use" to describe computer operations in a computing system. These terms are high-level descriptions for operations performed by a computer and should not be confused with acts performed by a human being. The actual computer operations corresponding to these terms vary depending on implementation.

Computer-Readable Media

Any of the computer-readable media herein can be non-transitory (e.g., volatile memory such as DRAM or SRAM, nonvolatile memory such as magnetic storage, optical storage, or the like) and/or tangible. Any of the storing actions described herein can be implemented by storing in one or more computer-readable media (e.g., computer-readable storage media or other tangible media). Any of the things (e.g., data created and used during implementation) described as stored can be stored in one or more computer-readable media (e.g., computer-readable storage media or other tangible media). Computer-readable media can be limited to implementations not consisting of a signal.

Any of the methods described herein can be implemented by computer-executable instructions in (e.g., stored on, encoded on, or the like) one or more computer-readable media (e.g., computer-readable storage media or other tangible media) or one or more computer-readable storage devices (e.g., memory, magnetic storage, optical storage, or the like). Such instructions can cause a computing system to perform the method. The technologies described herein can be implemented in a variety of programming languages.

Example Cloud Computing Environment

Figure 19:
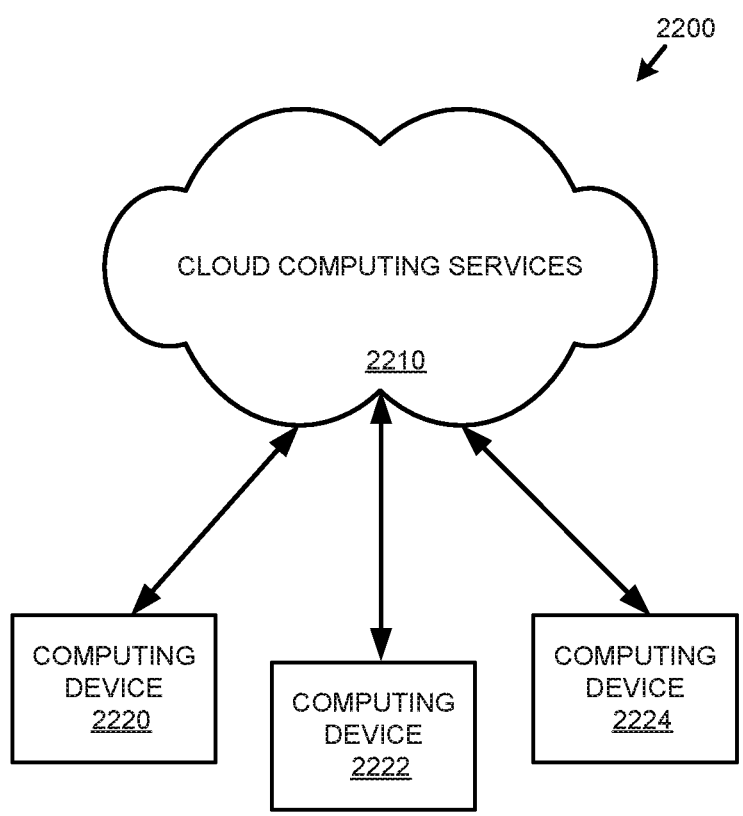
FIG. 19 is a block diagram of an example cloud computing environment that can be used in conjunction with the technologies described herein.

FIG. 19 depicts an example cloud computing environment 2200 in which the described technologies can be implemented, including, e.g., the systems described systems herein. The cloud computing environment 2200 comprises cloud computing services 2210. The cloud computing services 2210 can comprise various types of cloud computing resources, such as computer servers, data storage repositories, networking resources, etc. The cloud computing services 2210 can be centrally located (e.g., provided by a data center of a business or organization) or distributed (e.g., provided by various computing resources located at different locations, such as different data centers and/or located in different cities or countries).

The cloud computing services 2210 are utilized by various types of computing devices (e.g., client computing devices), such as computing devices 2220, 2222, and 2224. For example, the computing devices (e.g., 2220, 2222, and 2224) can be computers (e.g., desktop or laptop computers), mobile devices (e.g., tablet computers or smart phones), or other types of computing devices. For example, the computing devices (e.g., 2220, 2222, and 2224) can utilize the cloud computing services 2210 to perform computing operations (e.g., data processing, data storage, and the like).

In practice, cloud-based, on-premises-based, or hybrid scenarios can be supported.

Additional Examples

Additional examples based on principles described herein are enumerated below.

Further examples falling within the scope of the subject matter can be configured by, for example, taking one feature of an example in isolation, taking more than one feature of an example in combination, or combining one or more features of one example with one or more features of one or more other examples.

Example 1: A system comprises an exercise machine and a computing device coupled to the exercise machine. The computing device comprises a display memory, and a processor coupled to the memory, wherein the memory stores instructions that when executed by the processor causes the computing device to perform operations. The operations can include presenting a metrics bar within a graphical user interface of the display in an initial state, the metrics bar comprising a display area for one or more metrics; detecting a start of a first workout experience by a user on the exercise machine; in response to detecting the start of the first workout experience, retrieving a first set of metrics to display in the metrics bar from stored user preferences data associated with the user, wherein the first set of metrics is associated with a first workout experience profile comprising a type of the first workout experience, a type of workout associated with the first workout experience, and a type of the exercise machine; displaying the first set of metrics in the display area of the metrics bar during the first workout experience; detecting a start of a second workout experience by the user on the exercise machine; in response to detecting the start of the second workout experience, retrieving a second set of metrics in the metrics bar from the stored user preferences data associated with the user, wherein the second set of metrics is associated with a second workout experience profile comprising a type of the second workout experience, a type of workout associated with the second workout experience, and the type of the exercise machine; and displaying the second set of metrics in the display area of the metrics bar during the second workout experience.

Example 2: A system according to Example 1, wherein the operations can further include receiving a modification from the user to the first set of metrics during the first workout experience; storing the modified first set of metrics in the stored user preferences data, wherein the first set of modified metrics is associated with the type of the first workout experience, the workout type of the first workout experience, and the type of the exercise machine; and displaying the modified first set of metrics in the display area of the metrics bar during the first workout experience.

Example 3: A system according to Example 2, wherein receiving the modification from the user to the first set of metrics during the first workout experience comprises receiving a change to a display setting of a given metric in the first set of metrics.

Example 4: A system according to any one of Examples 1 to 3, wherein the operations can further include receiving a workout event from the exercise machine, determining a new value for a given metric included in the first set of metrics based on the workout event, updating the first set of metrics based on the new value of the given metric, and displaying the updated first set of metrics in the display area of the metrics bar during the first workout experience.

Example 5: A system according to any one of Examples 1 to 4, wherein the computing device is a console attached to the exercise machine.

Example 6: A system according to any one of Examples 1 to 4, wherein the computing device is a portable device communicatively coupled to the exercise machine.

Example 7: A method of operating an exercise machine comprises presenting a metrics bar within a graphical user interface of the display in an initial state, the metrics bar comprising a display area for one or more metrics; detecting a start of a first workout experience by a user on the exercise machine; in response to detecting the start of the first workout experience, retrieving a first set of metrics to display in the metrics bar from stored user preferences data associated with the user, wherein the first set of metrics is associated with a first workout experience profile comprising a type of the first workout experience, a type of workout associated with the first workout experience, and a type of the exercise machine; displaying the first set of metrics in the display area of the metrics bar during the first workout experience; detecting a start of a second workout experience by the user on the exercise machine; in response to detecting the start of the second workout experience, retrieving a second set of metrics in the metrics bar from the stored user preferences data associated with the user, wherein the second set of metrics is associated with a second workout experience profile comprising a type of the second workout experience, a type of workout associated with the second workout experience, and the type of the exercise machine; and displaying the second set of metrics in the display area of the metrics bar during the second workout experience.

Example 8: A method according to Example 7, wherein presenting the metrics bar within the graphical user interface of the display in the initial state comprises presenting the metrics bar without displaying any metrics in the display area of the metrics bar.

Example 9: A method according to Example 8, further comprising displaying a rotating message in the display area of the metrics bar prior to displaying the first set of metrics in the display area of the metrics bar.

Example 10: A method according to any one of Examples 7-9, further comprising detecting an end of the first workout experience and removing the first set of metrics from the display area of the metrics bar.

Example 11: A method according to any one of Examples 7-10, further comprising prior to displaying the first set of metrics in the display area of the metrics bar during the first workout experience, displaying a default set of metrics in the display area of the metrics bar.

Example 12: A method according to any one of Examples 7-10, further comprising displaying a default set of metrics in the display area of the metrics bar in addition to the first set of metrics displayed in the display area of the metrics bar during the first workout experience.

Example 13: A method according to any one of claims Example 7-12, further comprising receiving a workout event from the exercise machine, determining a new value for a given metric included in the first set of metrics based on the workout event, updating the first set of metrics based on the new value of the given metric, and displaying the updated first set of metrics in the display area of the metrics bar during the first workout experience.

Example 14: A method according to any one of Examples 7-13, further comprising receiving a modification from the user to the first set of metrics during the first workout experience; storing the modified first set of metrics in the stored user preferences data, wherein the first set of modified metrics is associated with the type of the first workout experience, the workout type of the first workout experience, and the type of the exercise machine; displaying the modified first set metrics in the display area of the metrics bar during the first workout experience.

Example 15: A method according to Example 14, wherein receiving the modification from the user to the first set of metrics during the first workout experience comprises receiving a change to a display setting of a given metric in the first set of metrics.

Example 16: A method according to Example 15, wherein receiving the change to the display setting of the given metric in the first set of metrics comprises receiving a request for a menu of configurable metrics associated with the type of workout associated with the first workout experience; presenting the menu of configurable metrics within the graphical user interface; and detecting the change to the display setting of the given metric from a user interaction with the menu.

Example 17: A method according to any one of Examples 7-16, wherein detecting the start of the first workout experience comprises detecting movement of a movable element of the exercise machine.

Example 18: A method according to any one of Examples 7-17, wherein presenting the metrics bar within the graphical user of the display comprises detecting a screen size and a screen orientation of the display and adjusting a number of rows of the display area of the modular metrics bar based on the screen size and the screen orientation.

Example 19: A method according to any one of Examples 7-18, further comprising presenting a workout experience screen view associated with the first workout experience within the graphical user interface during the first workout experience, wherein the modular metrics bar is floated or anchored relative to the first workout experience screen view within the graphical user interface.

Example 20: One or more non-transitory computer-readable media comprising computer-executable instructions that, when executed, cause a computing system to perform operations comprising: presenting a metrics bar within a graphical user interface of the display in an initial state, the metrics bar comprising a display area for one or more metrics; detecting a start of a first workout experience by a user on the exercise machine; in response to detecting the start of the first workout experience, retrieving a first set of metrics to display in the metrics bar from stored user preferences data associated with the user, wherein the first set of metrics is associated with a first workout profile comprising a workout experience type associated with the first workout experience, a workout type associated with the first workout experience, and a type of the exercise machine; displaying the first set of metrics in the display area of the metrics bar during the first workout experience; receiving a modification form the user to the first set of metrics during the first workout experience; storing the modified first set of metrics in the stored user preferences data, wherein the first set of modified metrics is associated with the type of the first workout experience, the workout type of the first workout experience, and the type of the exercise machine; displaying the modified first set of metrics in the display area of the metrics bar during the first workout experience; detecting a start of a second workout experience by the user on the exercise machine; in response to detecting the start of the second workout experience, retrieving a second set of metrics in the metrics bar from the stored user preferences data associated with the user, wherein the second set of metrics is associated with a second workout experience profile comprising a type of the second workout experience, a type of workout associated with the second workout experience, and the type of the exercise machine; and displaying the second set of metrics in the display area of the metrics bar during the second workout experience.

The invention claimed is:

1. A system comprising:
an exercise machine; and
a computing device coupled to the exercise machine, the computing device comprising a display, memory, and a processor coupled to the memory, wherein the memory stores instructions that when executed by the processor causes the computing device to perform operations comprising:
  detecting a start of a first workout experience by a user on the exercise machine, wherein the first workout experience is associated with a first type of workout experience;
  in response to detecting the start of the first workout experience, retrieving a first set of metrics to display in a metrics bar from stored user preferences data associated with a user, wherein the metrics bar comprises a display area and is presented within a graphical user interface of the display, and the first set of metrics is associated with a first workout experience profile comprising the first type of the first-workout experience, a type of workout associated with the first workout experience, and a type of the exercise machine;
  displaying the first set of metrics in the display area of the metrics bar during the first workout experience;
  detecting a start of a second workout experience on the exercise machine, wherein the second workout experience is associated with a second type of workout experience different from the first type of workout experience;
  in response to detecting the start of the second workout experience, retrieving a second set of metrics to display in the metrics bar from the stored user preferences data associated with the user, wherein the second set of metrics is associated with a second workout experience profile comprising the second type of workout experience, a type of workout associated with the second workout experience, and the type of the exercise machine; and
  displaying the second set of metrics in the display area of the metrics bar during the second workout experience,
  wherein the first set of metrics are different from the second set of metrics,
  wherein the first type of workout experience and the second type of workout experience are each configured to present, on the graphical user interface, one of a streaming video, a fitness training video, a video simulation, or a program tachometer.

2. The system of claim 1, wherein the operations further comprise:
  receiving a modification to the first set of metrics during the first workout experience;
  storing modified first set of metrics in the stored user preferences data in association with the first workout experience profile; and
  displaying the modified first set of metrics in the display area of the metrics bar during the first workout experience.

3. The system of claim 2, wherein receiving the modification to the first set of metrics during the first workout experience comprises receiving a change to a display setting of a given metric in the first set of metrics.

4. The system of claim 1, wherein the operations further comprise:
  receiving a workout event from the exercise machine, determining a new value for a given metric included in the first set of metrics based on the workout event, updating the first set of metrics based on the new value of the given metric, and displaying the updated first set of metrics in the display area of the metrics bar during the first workout experience.

5. The system of claim 1, wherein the computing device is a console attached to the exercise machine.

6. The system of claim 1, wherein the computing device is a portable device communicatively coupled to the exercise machine.

7. A method of operating an exercise machine, the method comprising:
  presenting a metrics bar within a graphical user interface of a display in an initial state, the metrics bar comprising a display area, wherein the display area shows neither name nor value of any metric when the metrics bar is in the initial state;
  detecting a start of a first workout experience on the exercise machine;
  in response to detecting the start of the first workout experience, retrieving a first set of metrics from stored user preferences data associated with a user, wherein the first set of metrics is associated with a first workout experience profile comprising a type of the first workout experience, a type of workout associated with the first workout experience, and a type of the exercise machine;
  displaying the first set of metrics in the display area of the metrics bar during the first workout experience;
  detecting a selection of a second workout experience different from the first workout experience;
  responsive to detecting the selection of the second workout experience, removing the first set of metrics from the display area of the metrics bar so that the metrics bar returns to the initial state;
  detecting a start of the second workout experience on the exercise machine;
  in response to detecting the start of the second workout experience, retrieving a second set of metrics from the stored user preferences data associated with the user, wherein the second set of metrics is associated with a second workout experience profile comprising a type of the second workout experience, a type of workout associated with the second workout experience, and the type of the exercise machine; and displaying the second set of metrics in the display area of the metrics bar during the second workout experience, wherein the first set of metrics are different from the second set of metrics.

8. The method of claim 7, wherein presenting the metrics bar within the graphical user interface of the display in the initial state comprises presenting the metrics bar without displaying any metrics in the display area of the metrics bar.

9. The method of claim 8, further comprising displaying a rotating message in the display area of the metrics bar prior to displaying the first set of metrics in the display area of the metrics bar.

10. The method of claim 7, further comprising:
detecting an end of the first workout experience; and
removing the first set of metrics from the display area of the metrics bar.

11. The method of claim 7, further comprising receiving a workout event from the exercise machine, determining a new value for a given metric included in the first set of metrics based on the workout event, updating the first set of metrics based on the new value of the given metric, and displaying the updated first set of metrics in the display area of the metrics bar during the first workout experience.

12. The method of claim 7, further comprising:
receiving a modification to the first set of metrics during the first workout experience;
storing modified first set of metrics in the stored user preferences data, wherein the modified first set of metrics is associated with the first workout experience profile; and
displaying the modified first set metrics in the display area of the metrics bar during the first workout experience.

13. The method of claim 12, wherein receiving the modification to the first set of metrics during the first workout experience comprises receiving a change to a display setting of a given metric in the first set of metrics.

14. The method of claim 13, wherein receiving the change to the display setting of the given metric in the first set of metrics comprises:
receiving a request for a menu of configurable metrics associated with the type of workout associated with the first workout experience;
presenting the menu of configurable metrics within the graphical user interface; and
detecting the change to the display setting of the given metric from a user interaction with the menu.

15. The method of claim 7, wherein detecting the start of the first workout experience comprises detecting movement of a movable element of the exercise machine.

16. The method of claim 7, wherein presenting the metrics bar within the graphical user of the display comprises detecting a screen size and a screen orientation of the display and adjusting a number of rows of the display area of the metrics bar based on the screen size and the screen orientation.

17. The method of claim 7, further comprising presenting a workout experience screen view associated with the first workout experience within the graphical user interface during the first workout experience, wherein the metrics bar is floated or anchored relative to the first workout experience screen view within the graphical user interface.

18. The method of claim 7, wherein detecting the start of the second workout experience comprises detecting that a screen associated with the second workout experience is present within the graphical user interface.

19. The method of claim 7, wherein detecting the start of the second workout experience comprises detecting that the user selects a button from the metrics bar or detecting movement of the user after conclusion of the first workout experience.

20. One or more non-transitory computer-readable media comprising computer-executable instructions that, when executed, cause a computing system to perform operations comprising:
presenting a metrics bar within a graphical user interface of a display of an exercise machine in an initial state, the metrics bar comprising a display area, wherein the display area shows neither name nor value of any metric when the metrics bar is in the initial state;
detecting a start of a first workout experience on the exercise machine;
in response to detecting the start of the first workout experience, retrieving a first set of metrics from stored user preferences data associated with a user, wherein the first set of metrics is associated with a first workout profile comprising a workout experience type associated with the first workout experience, a workout type associated with the first workout experience, and a type of the exercise machine;
displaying the first set of metrics in the display area of the metrics bar during the first workout experience;
receiving a modification to the first set of metrics during the first workout experience;
storing modified first set of metrics in the stored user preferences data, wherein the modified first set of metrics is associated with the type of the first workout experience, the workout type of the first workout experience, and the type of the exercise machine;
displaying the modified first set of metrics in the display area of the metrics bar during the first workout experience;
detecting a selection of a second workout experience different from the first workout experience;
responsive to detecting the selection of the second workout experience, removing the first set of metrics from the display area of the metrics bar so that the metrics bar returns to the initial state;
detecting a start of the second workout experience on the exercise machine;
in response to detecting the start of the second workout experience, retrieving a second set of metrics from the stored user preferences data associated with the user, wherein the second set of metrics is associated with a second workout experience profile comprising a type of the second workout experience, a type of workout associated with the second workout experience, and the type of the exercise machine; and
displaying the second set of metrics in the display area of the metrics bar during the second workout experience, wherein the first set of metrics are different from the second set of metrics.

* * * * *